United States Patent
Paterson et al.

(10) Patent No.: US 9,700,608 B2
(45) Date of Patent: *Jul. 11, 2017

(54) METHODS FOR CONSTRUCTING ANTIBIOTIC RESISTANCE FREE VACCINES

(71) Applicant: THE TRUSTEES OF THE UNIVERSITY OF PENNSYLVANIA, Philadelphia, PA (US)

(72) Inventors: Yvonne Paterson, Philadelphia, PA (US); Thorsten Verch, Blue Bell, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/296,973

(22) Filed: Oct. 18, 2016

(65) Prior Publication Data

US 2017/0028045 A1    Feb. 2, 2017

Related U.S. Application Data

(60) Continuation of application No. 14/537,599, filed on Nov. 10, 2014, now Pat. No. 9,492,527, which is a division of application No. 11/203,415, filed on Aug. 15, 2005, now Pat. No. 8,906,664.

(60) Provisional application No. 60/601,492, filed on Aug. 13, 2004.

(51) Int. Cl.

| A61K 39/02 | (2006.01) |
| A61K 39/00 | (2006.01) |
| A61K 35/74 | (2015.01) |
| C12N 9/10 | (2006.01) |
| C12N 9/16 | (2006.01) |
| C12N 9/90 | (2006.01) |
| C12N 15/52 | (2006.01) |
| C12N 15/74 | (2006.01) |
| A61K 39/12 | (2006.01) |
| C12N 7/00 | (2006.01) |

(52) U.S. Cl.
CPC .......... *A61K 39/0011* (2013.01); *A61K 35/74* (2013.01); *A61K 39/12* (2013.01); *C12N 7/00* (2013.01); *C12N 9/1096* (2013.01); *C12N 9/16* (2013.01); *C12N 9/90* (2013.01); *C12N 15/52* (2013.01); *C12N 15/74* (2013.01); *C12Y 206/01* (2013.01); *C12Y 206/01021* (2013.01); *C12Y 501/01001* (2013.01); *A61K 2039/523* (2013.01); *A61K 2039/585* (2013.01); *C12N 2710/00034* (2013.01); *C12N 2710/20033* (2013.01)

(58) Field of Classification Search
None
See application file for complete search history.

(56) References Cited

U.S. PATENT DOCUMENTS

| 4,458,066 A | 7/1984 | Caruthers et al. |
| 5,595,756 A | 1/1997 | Bally et al. |
| 5,922,583 A | 7/1999 | Morsey |
| 6,099,848 A | 8/2000 | Frankel et al. |
| 6,767,542 B2 | 7/2004 | Paterson et al. |
| 2002/0102722 A1 | 8/2002 | Lo et al. |
| 2005/0118184 A1 | 6/2005 | Paterson et al. |

FOREIGN PATENT DOCUMENTS

| JP | 2002-253212 | 10/2002 |
| JP | 2002-253253 | 10/2002 |
| WO | WO 90/09449 | 8/1990 |
| WO | WO 99/25376 | 5/1999 |
| WO | WO 01/72329 | 10/2001 |
| WO | WO 03/092600 | 11/2003 |
| WO | WO 03/097838 | 11/2003 |
| WO | WO 2005/026364 | 3/2005 |
| WO | WO 2006/017856 | 2/2006 |

OTHER PUBLICATIONS

Abachin et al., 2002, "Formation of D-alanyl-lipoteichoic acid is required for adhesion and virulence of Listeria monocytogenes", Mol. Microbiol. 43:1-14.
Alexander et al., 1993, "Characterization of an aromatic amino acid-dependent Listeria monocytogenes mutant: attenuation, persistence, and ability to produce protective immunity in mice", Infection and Immunity 61:2245-2248.
Angelakopoulos et al., "Safety and shedding of an attenuated strain of listeria monocytogenes with a deletion of actA/plcB in adult volunteers: a dose escalation study of oral innoculation", Infection and Immunity 2002, 70(7): 3592-3601.
Beaucage et al., 1981, "Deoxynucleoside Phosphoramidites—A New Class of Key Intermediates for Deoxypoylnucleotide Synthesis", Tetra. Lett. 22:1859-1862.
Bron et al., 2002, "Use of the alr Gene as a Food-Grade Selection Marker in Lactic Acid Bacteria", Applied and Environmental Microbiology, 68(11):5663-5670.
Brown et al., 1979, "Chemical Synthesis and Cloning of a Tyrosine tRNA Gene", Meth. Enzymol. 68:109-151.
Bruhn et al., "Listeria as a vaccine vector", Microbes and Infection 9, 2007, 1226-1235.
Brundage et al., 1993, "Expression and phosphorylation of the Listeria monocytogenes ActA protein in mammalian cells", Proc. Natl. Acad. Sci. USA 90:11890-11894.

(Continued)

*Primary Examiner* — Brian J Gangle

(74) *Attorney, Agent, or Firm* — Mark Cohen; Pearl Cohen; Zedek Latzer Baratz LLP

(57) ABSTRACT

The present invention provides *Listeria* vaccine strains that express a heterologous antigen and a metabolic enzyme, and methods of generating same.

18 Claims, 9 Drawing Sheets

(56) References Cited

OTHER PUBLICATIONS

Camilli et al., 1992, "Dual Roles of plcA in Listeria monocytogenes Pathogenesis", Mol. Microbiol. 8:143-157.
Camilli et al., 1991, "Listeria monocytogenes mutants lacking phosphatidylinositol-specific phospholipase C are avirulent", J. Exp. Med., 173:751-754.
Cenatiempo, 1986, "Prokaryotic Gene Expression in Vitro: Transcription—Translation Coupled Systems", Biochimie 68:505-516.
Cochlovius et al., "Oral DNA vaccination: Antigen uptake and presentation by dendritic cells elicits protective immunity", Immunology Letters, vol. 80, No. 2, 2002, pp. 89-96.
De Boer et al., 1989, "A division inhibitor and a topological specificity factor coded for by the minicell locus determine proper placement of the division septum in *E.coli*", Cell 56:641-649.
Definition of "Pest Sequence", accessed at: http://www.biology-text.com/definition.php?word=Pest+sequence on Jan. 22, 2007.
Dermer, 1994, "Another Anniversary for the War on Cancer", Bio/Technology, vol. 12, p. 320.
European Search Report for European Application No. 15167706.9 mailed Oct. 5, 2015.
Frankel et al., 1995, "Induction of cell-mediated immune responses to human immunodeficiency virus type 1 Gag protein by using Listeria monocytogenes as a live vaccine vector", J. Immunol. 1 55 :4775-4782.
Freshney, 1983, "Culture of Animal Cells, A Manual of Basic Technique", Alan R, Liss. Inc., pp. 3-4.
Gilman et al., 1984, "Isolation of sigma-28-specific promoters from *Bacillus subtilis* DNA", Gene 32:11-20.
Glenting, et al (2002)" A Plasmid Selection System in Luctococcus Lactis and Its Use for Gene Expression in L luctis and Human Kidney Fibroblasts." Applied and Environmental Microbiology vol. 68 5051-5056.
Glick, 1987, "Factors affecting the expression of foreign proteins in *Escherichia coli*", J. Ind. Microbiol. 1:277-282.
Gottesman, 1984, "Bacterial regulation: global regulatory networks", Ann. Rev. Genet. 18:415-442.
Greenspan et al., 1999, "Defining epitopes: It's not easy as it seems", Nature Biotechnology 7:936-937.
Gunn et al., 2001, "Two Listeria monocytogenes Vaccine Vectors That Express Different Molecular Forms of Human Papilloma Virus-16 (HPV-16) E7 Induce Qualitatively Different T Cell Immunity That Correlates with Their Ability to Induce Regression of Established Tumors Immortalized by HPV-16", J. Immunol. 167:6471-6479.
Gura, 1997, "Systems for Identifying New Drugs are Often Faulty", Science 278:1041-1042.
Harris et al., 1986, "Molecular basis for heterogeneity of the human p53 protein", Mol. Cell. Biol. 6:4650-4656.
Ikonomidis et al., 1994, "Delivery of a viral antigen to the class I processing and presentation pathway by Listeria monocytogenes", J. Exp. Med. 180: 2209-2218.
International Search Report of Application No. PCT/US08/04861 issued Sep. 29, 2008.
International Search Report of Application No. PCT/US05/28895 issued Jul. 5, 2006.
Keravala et al., Molecular Genetics and Genomics, Aug. 2006, 276 (2), p. 135-146.
Kohler, et al., 1991, "Expression of the iap gene coding for protein p60 of Listeria monocytogenes is controlled on the post-transcriptional level", J. Bacteriol 173: 4668-4674.
Lauer et al., 2002, "Construction, Characterization, and Use of Two Listeria monocytogenes Site-Specific Phage Integration Vectors", J. Bacteriol. 184:4177-4186.
Leitner et al., 2000, "DNA and RNA-based vaccines: principles, progress and prospects", Vaccine 18:765-777.

Li et al., "Conditional lethality yields a new vaccine strain of listeria monocytogenes for the induction of cell-mediated immunity", Infection and Immunity, 2005, 73(8): 5065-5073.
Lin et al. "Oral vaccination with recombinant Listeria monocytogenes expressing human papillomavirus type 16 E7 can cause tumor growth in mice to regress", Int J Cancer. Dec. 20, 2002;102(6):629-37.
Mata et al., 2001, "Evaluation of a recombinant Listeria monocytogenes expressing an HIV protein that protects mice against viral challenge", Vaccine 19:1435-1445.
Miller et al., 1995, "Targeted vectors for gene therapy", FASEB J., 9:190-199.
Narang et al., 1979, "Improved Phosphotriester Method for the Synthesis of Gene Fragments", Meth. Enzymol., 68:90-99.
Paglia et al., "Gene transfer in dendritic cells, induced by oral DNA vaccination with salmonella typhimurium, results in protective immunity against a murine fibrosarcoma", Blood, American Society of Hematology, vol. 92, No. 9, 1998, pp. 3172-3176.
Peters et al., "Enhancing the immunogenicity of bioengineered Listeria monocytogenes by passaging through live animal hosts." Vaccine, 21: 1187-1194, 2003.
Pilgrim et al., 2003, "Bactofection of mammalian cells by Listeria monocytogenes: improvement and mechanism of DNA delivery", Gene Ther., 10(24):2036-45.
Pucci et al., 1995, "*Staphylococcus haemolyticus* contains two D-glutamic acid biosynthetic activities, a glutamate racemase and a D-amino acid transaminase", J. Bacteriol. 177: 336-342.
Rechsteiner et al., "Pest sequences and regulation by proteolysis", Trends Biochem Sci. Jul. 1996;21(7):267-71.
Restifo et al., 2000, "The promise of nucleic acid vaccines", Gene Therapy, 7:89-92.
Rodriguez, "Nonviral DNA vectors for immunization and therapy: design and methods for their obtention", Journal of Molecular Medicine, vol. 82, No. 8, 2004, pp. 500-509.
Sizemore et al., 1995, "Attenuated Shigella as a DNA Delivery Vehicles for DNA-Mediated Immunization", Science 270:299-302.
Soubrier et al., "PCOR: A new design of plasmid vectors for nonviral gene therapy", Gene Therapy, vol. 6, 1990, pp. 1482-1488.
Strych et al., 2002, "Mutant analysis shows that alanine racemases from *Pseudomonas aeruginosa* and *Escherichia coli* are dimeric", J. Bacteriol. 184:4321-4325.
Tauch et al., 2002, "The alanine racemase gene alr is an alternative to antibiotic resistance genes in cloning systems for industrial Corynebacterium glutamicum strains", J. Biotechnol 99:79-91.
Thompson et al (1998) "Pathogenicity and immunogenicity of a Listeria monocytogenes strain that requires D-alanine for growth." Infec Immun 66: 3552-3561.
Ulmanen et al., 1985, "Transcription and translation of foreign genes in *Bacillus subtilis* by the aid of a secretion vector", J. Bacteriol., 162:176-182.
Verch et al., Nov. 2004, "Listeria monocytogenes-Based Antibiotic Resistance Gene-Free Antigen Delivery System Applicable to Other Bacterial Vectors and DNA Vaccines", Infection and Immunity, p. 6418-6425.
Ward et al., 1986, "Construction and Characterisation of a Series of Multi-copy Promoter-probe Plasmid Vectors for Streptomyces Using the Aminoglycoside Phosphotransferase Gene From Tn5 as Indicator", Mol. Gen. Genet. 203:468-478.
Wirth et al., 1986, "Highly efficient protoplast transformation system for *Streptococcus faecalis* and a new *Escherichia coli-S faecalis* shuttle vector", J. Bacteriol. 165(3):831-6.
Yaghmai et al., 2002 "Optimized regulation of gene expression using artificial transcription factors", Mol. Therapy, 5:685-694.
Sporn et al, "Chemoprevention of Cancer," Carcinogenesis, vol. 21 (2000), 525-530.
Auerbach et al (Cancer and Metastasis Reviews, 2000, 19: 167-172).
Gura T (Science, 1997,278(5340): 1041-1042.
Jain RK (Scientific American, Jul. 1994,58-65).
(http://www.biology-text.com/definition.php?word=Pest+sequence, accessed Jan. 22, 2007).

Figure 4
Figure 4A
Figure 4B
Figure 4C
Figure 4D Figure 6B                    Figure 6C Figure 7
Figure 7A
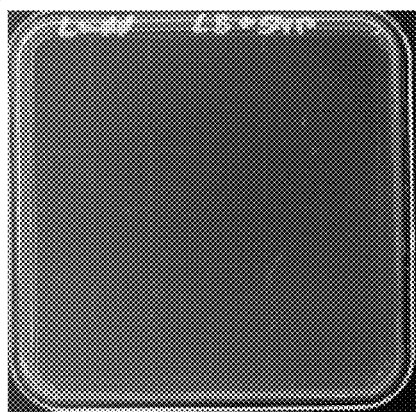
Figure 7B
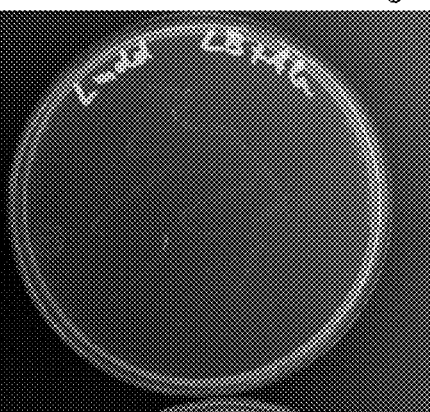
Figure 7C
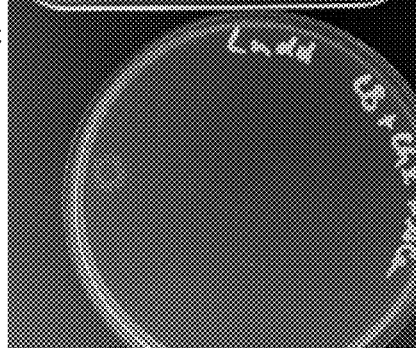
Figure 7D
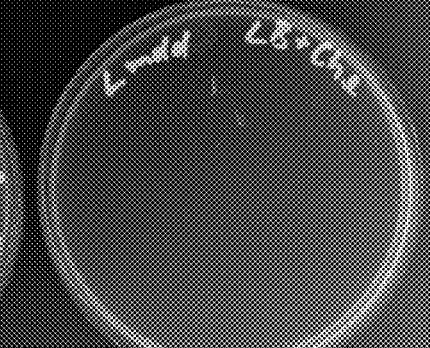

METHODS FOR CONSTRUCTING ANTIBIOTIC RESISTANCE FREE VACCINES

CROSS-REFERENCE TO RELATED APPLICATIONS

This application is a continuation of U.S. patent application Ser. No. 14/537,599, filed Nov. 10, 2014, which is a divisional of U.S. patent application Ser. No. 11/203,415, filed Aug. 15, 2005, which claims priority of U.S. Provisional Application Ser. No. 60/601,492, filed Aug. 13, 2004, all of which are incorporated by reference herein in their entirety.

STATEMENT REGARDING FEDERALLY SPONSORED RESEARCH OR DEVELOPMENT

This research was supported in part by U.S. Government funds (RAID NSC 715814 and CA69632) and the U.S. Government may therefore have certain rights in the invention.

FIELD OF INVENTION

The present invention provides *Listeria* vaccine strains that express a heterologous antigen and a metabolic enzyme, and methods of generating same.

BACKGROUND OF THE INVENTION

Vaccines represent the most beneficial and cost effective public health measure currently known. However, as the understanding of neoplasias and infectious diseases grows, it has become apparent that traditional vaccine strategies may not be completely effective. Traditional vaccines have employed killed or attenuated organisms or antigen subunits in order to elicit immunity in an animal. A limit with these approaches, especially with killed or subunit vaccines, is that the immune response is primarily humoral in nature, and therefore not effective in combating intracellular organism or tumors that require cell mediated immunity for their destruction. Similarly, attenuated or inactivated bacteria often only induce immunization for a short period of time and immunity is limited to a humoral response. Further, traditional attenuated or inactivated bacterial vaccines do not elicit the cytotoxic T-lymphocyte (CTL) immune response necessary for the lysis of tumor cells and cells infected with intracellular pathogens.

Viral vaccines are often used to induce a CTL response in a vaccine. Viral vaccines are usually pathogenic viruses attenuated by serial passage in cell culture or viruses killed through heat or chemical inactivation. Killed viruses are incapable of infecting cells, and thus, like subunit vaccines, primarily elicit a humoral immune response. Attenuated viruses are capable of infecting cells, and can induce a CTL response in an individual. However, attenuated virus vaccines are not without drawbacks. First, attenuating a virus is often a process of trial and error. Second, there is a serious safety issue in using attenuated viruses, especially in children, the elderly, and the immuno-compromised. A solution to the problems of traditional bacterial and viral vaccines exists with bacterial vaccine vectors such as *Listeria monocytogenes* (LM). LM is a beta hemolytic gram positive facultative intracellular microbe.

Three methods are currently used to express a heterologous antigen in *Listeria monocytogenes*, and include plasmid-based expression systems and chromosome expression systems. One chromosomal based method is described in Frankel et al. (1995, J. Immunol. 155:4775-4782) and Mata et al. (2001, Vaccine 19:1435-1445). Briefly, a gene encoding the antigen of interest is placed, along with a suitable promoter and signal sequence, between two regions of DNA homologous to a region of the *Listeria* chromosome. This homologous recombination allows specific integration of the antigen in the *Listeria* chromosome. The cassette comprising the antigen and the homologous DNA is ligated into a temperature sensitive plasmid incapable of replication at temperatures above 40° C. The plasmid further comprises drug resistance markers for selection and plasmid maintenance purposes. The manipulation and replication of this plasmid usually takes place in *E. coli*, because of its rapid replication and ease of transformation compared to *Listeria*. Because *Listeria* is a gram positive organism and *E. coli* is a gram negative organism, the drug resistance genes can be specific to each category of organism, or there may be two copies of the same drug resistance gene effective in both types of organism, but under the control of separate gram positive and gram negative promoters. After assembly, the plasmid is transformed into LM by direct conjugation with the *E. coli* comprising the plasmid, or by lysis and isolation of the plasmid from the *E. coli*, followed by electroporation of competent LM.

In order to integrate the plasmid into the desired region of the *Listeria* chromosome, the two-step allelic exchange method of Camilli et al. (1992, Mol. Microbiol. 8:143-157) is followed. Briefly, the *Listeria* is passaged at greater than 40° C. to prevent plasmid replication. Integration of the plasmid into the *Listeria* chromosome is selected by growth at 40° C. in the presence of a selecting drug, e.g. chloramphenicol. After selection of transformants, bacteria are passaged at 30° C. and selected for drug sensitivity to screen for *Listeria* in which excision of extraneous vector sequences has occurred. The disadvantage of this method is that the double allelic exchange method is time consuming and requires the selection of many clones in order to arrive at a suitable vaccine strain. A second chromosomal method of producing *Listeria* strains comprising a heterologous antigen is described by Lauer et al. (2002, J. Bacteriol. 184:4177-4186). This method does not require allelic exchange, but instead requires two phage-based integration vectors. This method utilizes one or two drug resistance genes, resulting in a *Listeria* organism comprising resistance to one or more drugs. The disadvantage of the methods of Lauer et al is the presence of drug resistance genes, which are not considered safe because of concern over the spread of antibiotic resistance to microorganisms previously susceptible to antibiotic therapy. Therefore, the presence of antibiotic resistance genes in a vaccine vector is considered a liability from a safety perspective.

A third method of expressing foreign antigen in *Listeria* is to express the antigen episomally from a plasmid. This method is described in Ikonomidis et al. (1994 J. Exp. Med. 180: 2209-2218) and Gunn et al. (2001, J Immunol 167: 6471-6479). This method has the advantage that the gene does not have to be integrated into the chromosome and can be expressed in multiple copies, which may enhance immunogenicity. However, in order to select for plasmid transformants and ensure the retention of the plasmid during propagation in vitro it is necessary to include two drug resistance genes on the plasmid, one for the construction of the plasmid in *E. coli* and one for the propagation of the transformed *Listeria monocytogenes*.

Thus, given the demonstrated uses of *Listeria* as a vaccine vector, methods for constructing *Listeria* vaccine vectors without antibiotic resistance, yet capable of eliciting a strong immune response, are needed in the field.

BRIEF SUMMARY OF THE INVENTION

The present invention provides *Listeria* vaccine strains that express a heterologous antigen and a metabolic enzyme, and methods of generating same.

In one embodiment, the present invention provides a method of engineering a *Listeria* vaccine strain to express a heterologous antigen, the method comprising contacting an auxotrophic *Listeria* strain with a plasmid, the plasmid comprising a first nucleic acid sequence encoding a polypeptide that comprises the heterologous antigen, and the plasmid further comprising a second nucleic acid sequence encoding a metabolic enzyme, whereby the auxotrophic *Listeria* strain takes up the plasmid, and whereby the metabolic enzyme complements a metabolic deficiency of the auxotrophic *Listeria* strain, thereby engineering a *Listeria* vaccine strain to express a heterologous antigen.

In another embodiment, the present invention provides a *Listeria* vaccine strain, comprising a plasmid, wherein the plasmid comprises a first nucleic acid sequence encoding a polypeptide, wherein the polypeptide comprises a protein antigen, and the plasmid further comprises a second nucleic acid sequence encoding a metabolic enzyme, whereby the metabolic enzyme complements an endogenous metabolic gene that is lacking in a chromosome of the *Listeria* vaccine strain, and whereby the plasmid is stably maintained in the *Listeria* vaccine strain in the absence of an antibiotic selection.

In another embodiment, the present invention provides a method of engineering a *Listeria* vaccine strain to express a heterologous antigen, the method comprising contacting an auxotrophic *Listeria* strain with a nucleic acid construct, the nucleic acid construct comprising a first nucleic acid sequence encoding a polypeptide that comprises the heterologous antigen, and the nucleic acid construct further comprising a second nucleic acid sequence encoding a metabolic enzyme, whereby the nucleic acid construct is incorporated into a genome of the auxotrophic *Listeria* strain, and whereby the metabolic enzyme complements a metabolic deficiency of the auxotrophic *Listeria* strain, thereby engineering a *Listeria* vaccine strain to express a heterologous antigen.

BRIEF DESCRIPTION OF THE DRAWINGS

FIG. 4A-4D depicts growth on Luria-Bertoni (LB) agar plates of *E. coli* strain MB2159 (alanine racemace negative) transformed with the pTV3 vector. Bacteria were plated on different media. FIG. 4A Upper left: agar alone. MB2159-TV3 grows. FIG. 4B Upper right: agar with alanine. MB2159-TV3 grows. FIG. 4C Lower left: agar with chloramphenicol. MB2159-TV3 do not grow because the CAT gene is missing. FIG. 4D Lower right: agar with chloramphenicol and alanine. MB2159-TV3 do not grow because the CAT gene is missing.

FIG. 5B Upper right: agar with alanine. MB2159 grows. FIG. 5C Lower left: agar with chloramphenicol. MB2159 does not grow. FIG. 5D Lower right. MB2159 does not grow.

FIG. 6A-6C depicts growth on LB-agar plates of LM strain Lmdd(−) transformed with the pTV3 vector. Bacteria were plated on different media: FIG. 6A Top: agar with streptomycin, no added alanine. Lmdd-pTV3 grow (the host strain 10403s is streptomycin resistant). FIG. 6B Lower left (agar with chloramphenicol) and FIG. 6C lower right (agar with chloramphenicol and alanine): Lmdd-pTV3 do not grow because the CAT gene is not present in pTV3.

FIG. 7A-7D depicts growth on LB-agar plates of LM strain Lmdd(−) without the pTV3 vector. FIG. 7A Upper left: agar with streptomycin. Lmdd (−) cannot grow in the absence of d-alanine. FIG. 7B Upper right: agar with alanine. Lmdd (−) grows. FIG. 7C Lower left (agar with chloramphenicol and alanine) and FIG. 7D lower right (agar with chloramphenicol): Lmdd(−) is sensitive to chloramphenicol and does not grow.

DETAILED DESCRIPTION OF THE INVENTION

Figure 1A:
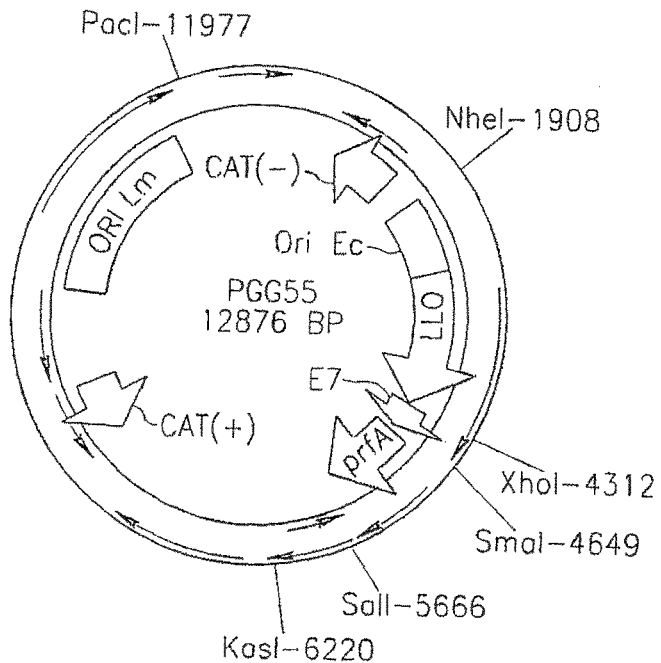
FIGS. 1A-1B is a schematic map of *E. coli-Listeria* shuttle plasmids pGG55 (left side) (FIG. 1A) and pTV3 (right side) (FIG. 1B). CAT(−): *E. coli* chloramphenicol transferase; CAT(+): *Listeria* chloramphenicol transferase; Ori Lm: replication origin for *Listeria*; Ori Ec: p15 origin of replication for *E. coli*, prfA: *Listeria* pathogenicity regulating factor A, LLO: C-terminally truncated listeriolysin O including its promoter; E7: HPV E7; p60-dal; expression cassette of p60 promoter and *Listeria* dal gene. Selected restriction sites are also depicted.

The present invention provides *Listeria* vaccine strains that express a heterologous antigen and a metabolic enzyme, and methods of generating same.

In one embodiment, the present invention provides a method of engineering a *Listeria* vaccine strain to express a heterologous antigen, the method comprising contacting an auxotrophic *Listeria* strain with a plasmid, the plasmid comprising a first nucleic acid sequence encoding a polypeptide that comprises the heterologous antigen, and the plasmid further comprising a second nucleic acid sequence encoding a metabolic enzyme, whereby the auxotrophic *Listeria* strain takes up the plasmid, and whereby the metabolic enzyme complements a metabolic deficiency of the auxotrophic *Listeria* strain, thereby engineering a *Listeria* vaccine strain to express a heterologous antigen.

In another embodiment, the present invention provides a method of engineering a *Listeria* vaccine strain to express a heterologous antigen, the method comprising transforming an auxotrophic *Listeria* strain with a plasmid comprising a first nucleic acid encoding the heterologous antigen and a second nucleic acid encoding a metabolic enzyme, whereby the metabolic enzyme complements a metabolic deficiency of the auxotrophic *Listeria* strain, thereby engineering a *Listeria* vaccine strain to express a heterologous antigen.

"Transforming," in one embodiment, is used identically with the term "transfecting," and refers to engineering a bacterial cell to take up a plasmid or other heterologous DNA molecule. In another embodiment, "transforming" refers to engineering a bacterial cell to express a gene of a plasmid or other heterologous DNA molecule. Each possibility represents a separate embodiment of the present invention.

As demonstrated by the data provided herein, a bacterial vaccine vector comprising a plasmid that expresses an antigen induces a stronger immune response than a fusion protein comprising an antigen expressed from the bacterial chromosome. Thus, the present invention discloses, for the first time, a bacterial vaccine vector that expresses a protein antigen and lacks antibiotic resistance genes.

In another embodiment, the plasmid of methods and compositions of the present invention further comprises a transcription factor. In another embodiment, the transcription factor is lacking in the auxotrophic *Listeria* strain or in the bacteria chromosome of a *Listeria* strain of the present invention. In one embodiment, the transcription factor is prfA (Examples herein). In another embodiment, the transcription factor is any other transcription factor known in the art.

In one embodiment, the metabolic gene, transcription factor, etc. is lacking in a chromosome of the bacterial strain. In another embodiment, the metabolic gene, transcription factor, etc. is lacking in all the chromosomes of the bacterial strain. In another embodiment, the metabolic gene, transcription factor, etc. is lacking in the genome of the bacterial strain.

In one embodiment, the transcription factor is mutated in the chromosome. In another embodiment, the transcription factor is deleted from the chromosome. Each possibility represents a separate embodiment of the present invention.

In one embodiment, the transcription factor is mutated in the chromosome. In another embodiment, the transcription factor is deleted from the chromosome. Each possibility represents a separate embodiment of the present invention.

In another embodiment, the plasmid of methods and compositions of the present invention does not confer antibiotic resistance to the *Listeria* vaccine strain. In another embodiment, the plasmid does not contain an antibiotic resistance gene. Each possibility represents a separate embodiment of the present invention.

In another embodiment of methods and compositions of the present invention, a polypeptide encoded by a nucleic acid sequence thereof is a fusion protein comprising the heterologous antigen and an additional polypeptide. In one embodiment, the additional polypeptide is a non-hemolytic fragment of an LLO protein (Examples herein). In another embodiment, the additional polypeptide is a PEST sequence. In another embodiment, the additional polypeptide is an ActA protein or a fragment thereof. ActA proteins and fragments thereof augment antigen presentation and immunity in a similar fashion to LLO.

In another embodiment, the first nucleic acid sequence of methods and compositions of the present invention is operably linked to a promoter/regulatory sequence. In another embodiment, the second nucleic acid sequence is operably linked to a promoter/regulatory sequence. In another embodiment, each of the nucleic acid sequences is operably linked to a promoter/regulatory sequence. Each possibility represents a separate embodiment of the present invention.

In another embodiment, the promoter/regulatory sequence of the second nucleic acid sequence functions in *E. coli*, thereby enabling stable maintenance of the plasmid in the *E. coli* strain. In another embodiment, the second nucleic acid sequence is expressed in an *E. coli* strain upon transfecting the *E. coli* strain with a plasmid of the present invention, thereby enabling stable maintenance of the plasmid in the *E. coli* strain.

In another embodiment of methods and compositions of the present invention, a metabolic enzyme encoded by a nucleic acid sequence thereof is an amino acid metabolism enzyme. In another embodiment, the metabolic enzyme is an alanine racemase (dal) enzyme. In another embodiment, the metabolic enzyme is a D-amino acid transferase enzyme (dat). The LM dal and dat genes were cloned and isolated from LM as described in Thompson et al (Infec Immun 66: 3552-3561, 1998).

In another embodiment, a dal gene utilized in the present invention has the sequence set forth in GenBank Accession Number AF038438. In another embodiment, the dal gene is any another dal gene known in the art. Each possibility represents a separate embodiment of the present invention.

In another embodiment, a dat gene utilized in the present invention has the sequence set forth in GenBank Accession Number AF038439. In another embodiment, the dat gene is any another dat gene known in the art. Each possibility represents a separate embodiment of the present invention.

Bacteria auxotrophic for D-alanine synthesis are well known in the art, and are described in, for example, *E. coli*, (Strych et al, 2002, J. Bacteriol. 184:4321-4325), *Corynebacterium glutamicum* (Tauch et al, 2002, J. Biotechnol 99:79-91), and *Listeria monocytogenes* (Frankel et al, U.S. Pat. No. 6,099,848)), *Lactococcus* species and *Lactobacillus* species Bron et al., (2002, Appl Environ Microbiol, 68: 5663-70).

In another embodiment, the present invention provides a *Listeria* vaccine strain, comprising a plasmid, wherein the plasmid comprises a first nucleic acid sequence encoding a polypeptide, wherein the polypeptide comprises a protein antigen, and the plasmid further comprises a second nucleic acid sequence encoding a metabolic enzyme, whereby the metabolic enzyme complements an endogenous metabolic gene that is lacking in a chromosome of the *Listeria* vaccine strain, and whereby the plasmid is stably maintained in the *Listeria* vaccine strain in the absence of an antibiotic selection.

In one embodiment, the endogenous metabolic gene is mutated in the chromosome. In another embodiment, the endogenous metabolic gene is deleted from the chromosome. Each possibility represents a separate embodiment of the present invention.

In another embodiment, the present invention provides a method of engineering a *Listeria* vaccine strain to express a heterologous antigen, the method comprising contacting an auxotrophic *Listeria* strain with a nucleic acid construct, the nucleic acid construct comprising a first nucleic acid sequence encoding a polypeptide that comprises the heterologous antigen, and the nucleic acid construct further comprising a second nucleic acid sequence encoding a metabolic enzyme, whereby the nucleic acid construct is incorporated into a genome of the auxotrophic *Listeria* strain, and whereby the metabolic enzyme complements a metabolic deficiency of the auxotrophic *Listeria* strain, thereby engineering a *Listeria* vaccine strain to express a heterologous antigen.

In one embodiment, the nucleic acid construct does not contain a *Listeria* replication region. Thus, only *Listeria* that contain a copy that is integrated into the genome are selected upon growth in LB media. In another embodiment, the nucleic acid construct contains a *Listeria* replication region. Each possibility represents a separate embodiment of the present invention.

In one embodiment, the nucleic acid construct contains an integration site. In one embodiment, the site is a PSA attPP' integration site. In another embodiment, the site is any another integration site known in the art. Each possibility represents a separate embodiment of the present invention.

In another embodiment, the nucleic acid construct contains an integrase gene. In another embodiment, the integrase gene is a PSA integrase gene. In another embodiment, the integrase gene is any other integrase gene known in the art. Each possibility represents a separate embodiment of the present invention.

In another embodiment, the integrase gene is expressed under the control of the *Listeria* p60 promoter. In another embodiment, the integrase gene is expressed under the control of any other promoter that functions in *Listeria*. Each possibility represents a separate embodiment of the present invention.

In one embodiment, the nucleic acid construct is a plasmid. In another embodiment, the nucleic acid construct is a shuttle plasmid. In another embodiment, the nucleic acid construct is any other type of nucleic acid construct known in the art. Each possibility represents a separate embodiment of the present invention.

In another embodiment, the step of incorporating the nucleic acid construct into the genome of the auxotrophic *Listeria* strain utilizes two-step allelic exchange. In another embodiment, the step of incorporating utilizes a phage-based integration vector. In another embodiment, the step of incorporating utilizes any other integration method known in the art.

In another embodiment, the step of incorporating the nucleic acid construct utilizes a prophage integration site of the auxotrophic *Listeria* strain. In another embodiment, the step of incorporating utilizes any other integration site known in the art. Each possibility represents a separate embodiment of the present invention.

Each possibility represents a separate embodiment of the present invention.

In another embodiment, the present invention provides a *Listeria monocytogenes*-*Escherichia coli* shuttle plasmid that is retained by complementation of mutant strains deficient in a metabolic gene both in vitro and in vivo. In one embodiment, the metabolic gene is a D-alanine racemase gene. In another embodiment, the metabolic gene is any other metabolic gene of known in the art. Each possibility represents a separate embodiment of the present invention.

In another embodiment, the present invention provides a method of attenuating a bacterial vaccine strain, comprising introducing into the strain a mutation in a gene encoding a metabolic enzyme and transfecting the strain with a plasmid containing a nucleotide sequence encoding the metabolic enzyme, thereby attenuating a bacterial vaccine strain.

In another embodiment, the present invention provides a method of attenuating a *Listeria* vaccine strain, comprising introducing into the strain a mutation in a gene encoding a metabolic enzyme and transfecting the strain with a plasmid containing a nucleotide sequence encoding the metabolic enzyme, thereby attenuating a metabolic enzyme vaccine strain.

In one embodiment, a metabolic gene methods and compositions of the present invention are expressed under an inducible promoter. In another embodiment, the promoter is a constitutive promoter. In another embodiment, the promoter is any other type of promoter known in the art. Each possibility represents a separate embodiment of the present invention.

In another embodiment, the present invention provides a bacterial vaccine strain constructed by the method of the present invention.

In another embodiment, the present invention provides a *Listeria* vaccine strain constructed by the method of the present invention.

In various embodiments, the antigen of methods and compositions of the present invention includes but is not limited to antigens from the following infectious diseases, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Japanese encephalitis (e.g., GenBank Accession No. E07883), dengue (e.g., GenBank Accession No. M24444), hantavirus, and AIDS (e.g., GenBank Accession No. U18552). Bacterial and parasitic antigens will be derived from known causative agents responsible for diseases including, but not limited to, diphtheria, pertussis (e.g., GenBank Accession No. M35274), tetanus (e.g., GenBank Accession No. M64353), tuberculosis, bacterial and fungal pneumonias (e.g., *Haemophilus influenzae, Pneumocystis carinii*, etc.), cholera, typhoid, plague, shigellosis, *salmonellosis* (e.g., GenBank Accession No. L03833), Legionnaire's Disease, Lyme disease (e.g., GenBank Accession No. U59487), malaria (e.g., GenBank Accession No. X53832), hookworm, onchocerciasis (e.g., GenBank Accession No. M27807), schistosomiasis (e.g., GenBank Accession No. L08198), trypanosomiasis, leshmaniasis, giardiasis (e.g., GenBank Accession No. M33641), amoebiasis, filariasis (e.g., GenBank Accession No. J03266), borreliosis, and trichinosis.

In other embodiments, the antigen is one of the following tumor antigens: any of the various MAGEs (Melanoma-Associated Antigen E), including MAGE 1 (e.g., GenBank Accession No. M77481), MAGE 2 (e.g., GenBank Accession No. U03735), MAGE 3, MAGE 4, etc.; any of the various tyrosinases; mutant ras; mutant p53 (e.g., GenBank Accession No. X54156 and AA494311); and p97 melanoma antigen (e.g., GenBank Accession No. M12154). Other tumor-specific antigens include the Ras peptide and p53 peptide associated with advanced cancers, the HPV 16/18 and E6/E7 antigens associated with cervical cancers, MUC 1-KLH antigen associated with breast carcinoma (e.g., Gen- Bank Accession No. J0365 1), CEA (carcinoembryonic antigen) associated with colorectal cancer (e.g., GenBank Accession No. X983 11), gp100 (e.g., GenBank Accession No. S73003) or MART1 antigens associated with melanoma, and the PSA antigen associated with prostate cancer (e.g., GenBank Accession No. X14810). The p53 gene sequence is known (See e.g., Harris et al. (1986) Mol. Cell. Biol., 6:4650-4656) and is deposited with GenBank under Accession No. M14694. Tumor antigens encompassed by the present invention further include, but are not limited to, Her-2/Neu (e.g. GenBank Accession Nos. M16789.1, M16790.1, M16791.1, M16792.1), NY-ESO-1 (e.g. GenBank Accession No. U87459), hTERT (aka telomerase) (GenBank Accession. Nos. NM003219 (variant 1), NM198255 (variant 2), NM 198253 (variant 3), and NM 198254 (variant 4), proteinase 3 (e.g. GenBank Accession Nos. M29142, M75154, M96839, X55668, NM 00277, M96628 and X56606) HPV E6 and E7 (e.g. GenBank Accession No. NC 001526) and WT-1 (e.g. GenBank Accession Nos. NM000378 (variant A), NM024424 (variant B), NM 024425 (variant C), and NM024426 (variant D)), Her-2/Neu (e.g. GenBank Accession Nos. M16789.1, M16790.1, M16791.1, M16792.1), NY-ESO-1 (e.g. GenBank Accession No. U87459), hTERT (aka telomerase) (GenBank Accession. Nos. NM003219 (variant 1), NM198255 (variant 2), NM 198253 (variant 3), and NM 198254 (variant 4), proteinase 3 (e.g. GenBank Accession Nos. M29142, M75154, M96839, X55668, NM 00277, M96628 and X56606) HPV E6 and E7 (e.g. GenBank Accession No. NC 001526) and WT-1 (e.g. GenBank Accession Nos. NM000378 (variant A), NM024424 (variant B), NM 024425 (variant C), and NM024426 (variant D)). Thus, the present invention can be used as immunotherapeutics for cancers including, but not limited to, cervical, breast, colorectal, prostate, lung cancers, and for melanomas.

Each of the above antigens represents a separate embodiment of the present invention.

In one embodiment, vectors of the present invention provide the benefits of a *Listeria* vaccine vector without the risk of increasing antibiotic resistance in bacterial organisms.

In another embodiment, an advantage of vaccine strains of the present invention is that the recombinant plasmids contained therein are not likely to be retained upon potential transfer to other bacteria in the gut. In another embodiment, the advantage is that the plasmids do not confer an evolutionary advantage on normal cells. In another embodiment, the advantage is that the plasmids do not contain active retention systems such as partition sequences. Thus, outside their deficient host cells, the plasmids will most likely be diluted out of the population and ultimately be eliminated over time. Each possibility represents a separate embodiment of the present invention.

In another embodiment, the present invention provides a kit comprising an antibiotic resistance free bacterial strain of the present invention, a pharmaceutically-acceptable carrier, an applicator, and an instructional material for use thereof.

In another embodiment, the present invention provides a kit comprising an antibiotic resistance free *Listeria* strain of the present invention, an applicator, and an instructional material for use thereof.

"Alanine racemase" refers, in one embodiment, to an enzyme that converts the L-isomer of the amino acid alanine into its D-isomer. In another embodiment, such enzymes are known by the EC number 5.1.1.1.

"Amino acid metabolism enzyme" refers, in one embodiment, to a peptide or protein that has a functional role in converting an amino acid from one form to another, such as, but not limited to, altering the stereochemistry of the amino acid, hydrolyzing or adding groups to an amino acid, cleaving amino acids, and the like. Each possibility represents a separate embodiment of the present invention.

The term "auxotrophic bacteria" refers, in one embodiment, to a bacteria strain that is not capable of growing or replicating without supplementation of a factor that will permit such growth or replication. Each factor represents a separate embodiment of the present invention.

"Fusion protein" refers, in one embodiment, to a protein that comprises two or more proteins linked together. In one embodiment, the proteins are linked by peptide bonds. In another embodiment, the proteins are linked by other chemical bonds. In another embodiment, the proteins are linked by with one or more amino acids between the two or more proteins, which may be referred to as a spacer. Each possibility represents a separate embodiment of the present invention.

"Homologous" refers, in one embodiment, to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. In another embodiment, the homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology. In another embodiment, "homology" is used synonymously with "identity." In another embodiment, when the terms "homology" or "identity" are used herein to refer to the nucleic acids and proteins, it should be construed to be applied to homology or identity at both the nucleic acid and the ammo acid sequence levels.

In another embodiment, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals or organisms. This can be readily carried out by using hybridization probes to identify the same genetic locus in a variety of individuals or organisms. Any and all such nucleotide variations and resulting amino acid polymorphisms or variations that are the result of natural allelic variation and that do not alter the functional activity are intended to be within the scope of the invention.

Describing two polynucleotides as "operably linked" means, in one embodiment, that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

"Promoter/regulatory sequence" refers, in one embodiment, to a nucleic acid sequence which is required for, or enhances, expression of a gene product operably linked to the promoter/regulatory sequence. In another embodiment, this sequence is the core promoter sequence. In another embodiment, this sequence also includes an enhancer sequence and other regulatory elements that are required for expression of the gene product.

I. *Listeria* Vaccine Strains

The particular *Listeria* strain employed will be apparent to the skilled artisan. Examples of *Listeria* strains which can be employed in the present invention includes *Listeria monocytogenes* (ATCC No. 15313). In other embodiments, attenuated *Listeria* strains, such as LM delta-actA mutant (Brundage et al, 1993, Proc. Natl. Acad. Sci., USA, 90:11890-11894), or *L. monocytogenes* delta-plcA (Camilli et al, 1991, J. Exp. Med., 173:751-754) are used in the present invention. In another embodiment, new attenuated *Listeria* strains are constructed by introducing one or more attenuating mutations, as will be understood by one of average skill in the art when equipped with the disclosure herein. Examples of such strains include, but are not limited to *Listeria* strains auxotrophic for aromatic amino acids (Alexander et al, 1993, Infection and Immunity 61:2245-2248) and mutant for the formation of lipoteichoic acids (Abachin et al, 2002, Mol. Microbiol. 43:1-14).

The skilled artisan, when equipped with the present disclosure and the methods herein, will readily understand that different transcriptional promoters, terminators, carrier vectors or specific gene sequences (e.g. those in commercially available cloning vectors) may be used successfully in methods and compostions of the present invention. As is contemplated in the present invention, these functionalities are provided in, for example, the commercially available vectors known as the pUC series. In another embodiment, non-essential DNA sequences (e.g. antibiotic resistance genes) are removed.

In another embodiment, a commercially available plasmid is used in the present invention. Such plasmids are available from a variety of sources, for example, Invitrogen (La Jolla, Calif.), Stratagene (La Jolla, Calif.), Clontech (Palo Alto, Calif.), or can be constructed using methods well known in the art. Another embodiment is a plasmid such as pCR2.1 (Invitrogen, La Jolla, Calif.), which is a prokaryotic expression vector with a prokaryotic origin of replication and promoter/regulatory elements to facilitate expression in a prokaryotic organism. In another embodiment, extraneous nucleotide sequences are removed to decrease the size of the plasmid and increase the size of the cassette that may be placed therein.

Such methods are well known in the art, and are described in, for example, Sambrook et al. (1989, Molecular Cloning: A Laboratory Manual, Cold Spring Harbor Laboratory Press, New York) and Ausubei et al. (1997, Current Protocols in Molecular Biology, Green & Wiley, New York).

Antibiotic resistance genes are used in the conventional selection and cloning processes commonly employed in molecular biology and vaccine preparation. Antibiotic resistance genes contemplated in the present invention include, but are not limited to, gene products that confer resistance to ampicillin, penicillin, methicillin, I streptomycin, erythromycin, kanamycin, tetracycline, cloramphenicol (CAT), neomycin, hygromycin, gentamicin and others well known in the art. Each gene represents a separate embodiment of the present invention.

Methods for transforming bacteria are well known in the art, and include calcium-chloride competent cell-based methods, electroporation methods, bacteriophage-mediated transduction, chemical, and physical transformation techniques (de Boer et al, 1989, Cell 56:641-649; Miller et al, 1995, FASEB J., 9:190-199; Sambrook et al. 1989, Molecular Cloning: A Laboratory Manual, Cold Spring Harbor Laboratory, New York; Ausubel et al., 1997, Current Protocols in Molecular Biology, John Wiley & Sons, New York; Gerhardt et al., eds., 1994, Methods for General and Molecular Bacteriology, American Society for Microbiology, Washington, D.C.; Miller, 1992, A Short Course in Bacterial Genetics, Cold Spring Harbor Laboratory Press, Cold Spring Harbor, N.Y.) In another embodiment, the *Listeria* vaccine strain of the present invention is transformed by electroporation. Each method represents a separate embodiment of the present invention.

Plasmids and other expression vectors useful in the present invention are described elsewhere herein, and can include such features as a promoter/regulatory sequence, an origin of replication for gram negative and gram positive bacteria, an isolated nucleic acid encoding a fusion protein and an isolated nucleic acid encoding an amino acid metabolism gene. Further, an isolated nucleic acid encoding a fusion protein and an amino acid metabolism gene will have a promoter suitable for driving expression of such an isolated nucleic acid. Promoters useful for driving expression in a bacterial system are well known in the art, and include bacteriophage lambda, the bla promoter of the beta-lactamase gene of pBR322, and the CAT promoter of the chloramphenicol acetyl transferase gene of pBR325. Further examples of prokaryotic promoters include the major right and left promoters of bacteriophage lambda ($P_L$ and $P_R$), the trp, recA, lacZ, lacI, and gal promoters of *E. coli*, the alpha-amylase (Ulmanen et al, 1985. J. Bacteriol. 162:176-182) and the S28-specific promoters of *B. subtilis* (Gilman et al, 1984 Gene 32:11-20), the promoters of the bacteriophages of *Bacillus* (Gryczan, 1982, In: The Molecular Biology of the *Bacilli*, Academic Press, Inc., New York), and *Streptomyces* promoters (Ward et al, 1986, Mol. Gen. Genet. 203:468-478). Additional prokaryotic promoters contemplated in the present invention are reviewed in, for example, Glick (1987, J. Ind. Microbiol. 1:277-282); Cenatiempo, (1986, Biochimie, 68:505-516); and Gottesman, (1984, Ann. Rev. Genet. 18:415-442). Further examples of promoter/regulatory elements contemplated in the present invention include, but are not limited to the *Listerial* prfA promoter, the *Listerial* hly promoter, the *Listerial* p60 promoter and the *Listerial* ActA promoter (GenBank Acc. No. NC_003210) or fragments thereof.

The gene expressed on a plasmid of the present invention comprises, in one embodiment, an isolated nucleic acid encoding a protein that complements the auxotrophic mutant. In another embodiment, if the auxotrophic bacteria is deficient in a gene encoding a vitamin synthesis gene (e.g. pantothenic acid) necessary for bacterial growth, the plasmid DNA comprises a gene encoding a protein for pantothenic acid synthesis. Thus, the auxotrophic bacteria, when expressing the gene on the plasmid, can grow in the absence of pantothenic acid, whereas an auxotrophic bacteria not expressing the gene on the plasmid cannot grow in the absence of pantothenic acid.

In another embodiment, the plasmid comprises a gene encoding an amino acid metabolism enzyme. Such enzymes metabolize amino acids such that they can be used for bacterial growth and replication processes, such as cell wall synthesis, protein synthesis, fatty acid metabolism, and the like. In another embodiment, an auxotrophic bacteria is deficient in the amino acid metabolism enzymes for D-glutamic acid, a cell wall component. D-glutamic acid synthesis is controlled by the dat gene, which is involved in the conversion of D-glu+pyr to alpha-ketoglutarate+D-ala, and the reverse reaction. D-glutamic acid synthesis is also controlled by the dga gene, and an auxotrophic mutant for D-glutamic acid synthesis will not grow in the absence of D-glutamic acid (Pucci et al, 1995, J Bacteriol. 177: 336-342). A further example includes a gene involved in the synthesis of diaminopimelic acid. Such synthesis genes encode beta-semialdehyde dehydrogenase, and when inactivated, renders a mutant auxotrophic for this synthesis pathway (Sizemore et al, 1995, Science 270: 299-302).

In another embodiment, a plasmid of methods and compositions of the present invention comprises a gene encoding a fusion protein. Fusion proteins comprising an antigen may be prepared by any suitable method, including, for example, cloning and restriction of appropriate sequences or direct chemical synthesis by methods discussed below. Alternatively, subsequences may be cloned and the appropriate subsequences cleaved using appropriate restriction enzymes. The fragments may then be ligated to produce the desired DNA sequence. In another embodiment, DNA encoding the antigen is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The antigen is ligated into a plasmid. Each method represents a separate embodiment of the present invention.

In another embodiment, the present invention further comprises a phage based chromosomal integration system for clinical applications. A host strain that is auxotrophic for essential enzymes, including, but not limited to, d-alanine racemase will be used, for example Lmdal(−)dat(−). In order to avoid a "phage curing step", a phage integration system based on PSA will be used (Lauer, et al., 2002 J Bacteriol, 184: 4177-4186). This requires, in another embodiment, continuous selection by antibiotics to maintain the integrated gene. Thus, in another embodiment, the current invention enables the establishment of a phage based chromosomal integration system that does not require selection with antibiotics. Instead, an auxotrophic host strain will be complemented.

The recombinant proteins of the present invention are synthesized, in another embodiment, using recombinant DNA methodology. This involves, in one embodiment, creating a DNA sequence that encodes the fusion protein, placing the DNA in an expression cassette, such as the plasmid of the present invention, under the control of a particular promoter/regulatory element, and expressing the protein. DNA encoding the fusion protein (e.g. non-hemolytic LLO/antigen) of the present invention may be prepared by any suitable method, including, for example, cloning and restriction of appropriate sequences or direct chemical synthesis by methods such as the phosphotriester method of Narang et al. (1979, Meth. Enzymol. 68: 90-99); the phosphodiester method of Brown et al. (1979, Meth. Enzymol 68: 109-151); the diethylphosphoramidite method of Beaucage et al. (1981, Tetra. Lett., 22: 1859-1862); and the solid support method of U.S. Pat. No. 4,458,066.

In another embodiment, chemical synthesis is used to produce a single stranded oligonucleotide. This single stranded oligonucleotide is converted, in various embodiments, into double stranded DNA by hybridization with a complementary sequence, or by polymerization with a DNA polymerase using the single strand as a template. One of skill in the art would recognize that while chemical synthesis of DNA is limited to sequences of about 100 bases, longer sequences may be obtained by the ligation of shorter sequences. In another embodiment, subsequences are cloned and the appropriate subsequences cleaved using appropriate restriction enzymes. The fragments are then be ligated to produce the desired DNA sequence.

In another embodiment, DNA encoding the fusion protein or the recombinant protein of the present invention may be cloned using DNA amplification methods such as polymerase chain reaction (PCR). Thus, the gene for non-hemolytic LLO is PCR amplified, using a sense primer comprising a suitable restriction site and an antisense primer comprising another restriction site, e.g. a non-identical restriction site to facilitate cloning. The same is repeated for the isolated nucleic acid encoding an antigen. Ligation of the non-hemolytic LLO and antigen sequences and insertion into a plasmid or vector produces a vector encoding non-hemolytic LLO joined to a terminus of the antigen. The two molecules are joined either directly or by a short spacer introduced by the restriction site.

In another embodiment, the molecules are separated by a peptide spacer consisting of one or more amino acids, generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity. In another embodiment, the nucleic acid sequences encoding the fusion or recombinant proteins are transformed into a variety of host cells, including *E. coli*, other bacterial hosts, such as *Listeria*, yeast, and various higher eukaryotic cells such as the COS, CHO and HeLa cells lines and myeloma cell lines. The recombinant fusion protein gene will be operably linked to appropriate expression control sequences for each host. Promoter/regulatory sequences are described in detail elsewhere herein. In another embodiment, the plasmid further comprises additional promoter regulatory elements, as well as a ribosome binding site and a transcription termination signal. For eukaryotic cells, the control sequences will include a promoter and an enhancer derived from e.g. immunoglobulin genes, SV40, cytomegalovirus, etc., and a polyadenylation sequence, and may include splice donor and acceptor sequences.

In another embodiment, a fusion protein of the present invention comprises, inter alia, an LM non-hemolytic LLO protein. The non-hemolytic LLO protein comprises, in one embodiment, about the first 400 to 441 amino acids of the 529 amino acid full-length LLO protein, the sequence of which is described in, for example, Mengaud et al, (1988, Infect. Immun. 56:766-772, GenBank Acc. No. P13128). The construction of a fusion protein comprising an antigen and a non-hemolytic LLO protein is described elsewhere herein, and in, for example, Gunn et al, (2001, J. Immunology 167: 6471-6479).

In another embodiment, a fusion protein of methods and compositions of the present invention comprises a Proline, Glutamic acid, Serine and Threonine rich (PEST) sequence, either from an LLO protein or from another organism, e.g. a prokaryotic organism.

In another embodiment, a fusion protein of methods and compositions of the present invention an Act A sequence from a *Listeria* organism. The construction and use of a fusion protein comprising a PEST sequence or an ActA sequence can proceed essentially as described herein and in U.S. Pat. No. 6,767,542, International Publication No. WO 01/72329 and U.S. application Ser. No. 10/835,662 of Paterson et al.

The antigens of these and other diseases are well known in the art, and the skilled artisan, when equipped with the present disclosure and the methods and techniques described herein will readily be able to construct a fusion protein comprising a non-hemolytic LLO protein and an antigen for use in the present invention. In another embodiment, in order to select for an auxotrophic bacteria comprising the plasmid, transformed auxotrophic bacteria are grown on a media that will select for expression of the amino acid metabolism gene. For example, in one embodiment, a bacteria auxotrophic for D-glutamic acid synthesis is transformed with a plasmid comprising a gene for D-glutamic acid synthesis, and the auxotrophic bacteria will grow in the absence of D-glutamic acid, whereas auxotrophic bacteria that have not been transformed with the plasmid, or are not expressing the plasmid encoding a protein for D-glutamic acid synthesis, will not grow. In another embodiment, a bacteria auxotrophic for D-alanine synthesis will grow in the absence of D-alanine when transformed and expressing the plasmid of the present invention if the plasmid comprises an isolated nucleic acid encoding an amino acid metabolism enzyme for D-alanine synthesis. Such methods for making appropriate media comprising or lacking necessary growth factors, supplements, amino acids, vitamins, antibiotics, and the like are well known in the art, and are available commercially (Becton-Dickinson, Franklin Lakes, N.J.). Each method represents a separate embodiment of the present invention.

In another embodiment, once the auxotrophic bacteria comprising the plasmid of the present invention have been selected on appropriate media, the bacteria are propagated in the presence of a selective pressure. Such propagation comprises growing the bacteria in media without the auxotrophic factor. The presence of the plasmid expressing an amino acid metabolism enzyme in the auxotrophic bacteria ensures that the plasmid will replicate along with the bacteria, thus continually selecting for bacteria harboring the plasmid. The skilled artisan, when equipped with the present disclosure and methods herein will be readily able to scale-up the production of the *Listeria* vaccine vector by adjusting the volume of the media in which the auxotrophic bacteria comprising the plasmid are growing.

EXPERIMENTAL DETAILS SECTION

Example 1

Elicitation of Immune Responses by Bacterial Vectors

Carrying Episomal Antigen-Encoding Constructs

Materials and Experimental Methods

Transformation and Selection

*E. coli* strain MB2159 was used for transformations, using standard protocols. Bacterial cells were prepared for electroporation by washing with $H_2O$.

Bacterial Culture and In Vivo Passaging of *Listeria*

*E. coli* were cultured following standard methods. *Listeria* were grown at 37° C., 250 rpm shaking in LB media (Difco, Detroit, Mich.). +50 µg/ml streptomycin, and harvested during exponential growth phase. For Lm-LLOE7, 37 µg/ml chloramphenicol was added to the media. For growth kinetics determinations, bacteria were grown for 16 hours in 10 ml of LB+antibiotics. The $OD_{600nm}$ was measured and culture densities were normalized between the strains. The culture was diluted 1:50 into LB+suitable antibiotics and D-alanine if applicable.

Passaging of LM in Mice $1 \times 10^8$ CFU were injected intraperitoneally (ip.) into C57BL/6 mice. On day three, spleens were isolated and homogenized in PBS. An aliquot of the spleen suspension was plated on LB plates with antibiotics as applicable. Several colonies were expanded and mixed to establish an injection stock.

Generation of Plasmid pGG55

The starting point for subcloning of pGG55 was the plasmid pDP1659. pDP1659 was generated by PCR (polymerase chain reaction)-amplifying from LM genomic DNA the DNA fragment encoding first 420 amino acids of LLO together with the upstream regulatory sequences and promoter, then ligating the fragment into pUC19. The DNA fragment encoding the NP antigen was PCR amplified, using plasmid pAPR501, provided by Dr. Peter Palese, as a template, and ligated into pUC19 as an in-frame translational fusion downstream of the LLO fragment. The fusion protein was then subcloned into pAM401, a shuttle vector able to replicate in both gram-negative and gram-positive bacteria (Wirth R, An F Y, Clewell D B. Highly efficient protoplast transformation system for *Streptococcus faecalis* and a new *Escherichia coli-S. faecalis* shuttle vector. J Bacteriol 165(3): 831-6, 1986). The hly promoter and gene fragment were generated using primers 5'-GGGGGCTAGC-CCTCCTTTGATTAGTATATTC-3' (SEQ ID NO: 3) and 5'-CTCCCTCGAGATCATAATTTACTTCATC-3' (SEQ ID NO: 4).

Next, plasmid pDP2028 was constructed by cloning the prfA gene into the SalI site of pDP1659. The prfA gene was PCR amplified using the following primers:

```
                                              (SEQ ID NO: 5)
5'-GACTACAAGGACGATGACCGACAAGTGATAACCCGGGAT

CTAAATAAATCCGTTT-3'
and (SEQ ID NO: 6)
5'-CCCGTCGACCAGCTCTTCTTGGTGAAG-3'.
``` pGG34 was next created from pDP2028 and pGG49. pGG49 contains an insert that consists of the hly-promoter, a gene encoding an N-terminal LLO fragment fused with HIV gp70, and the *Listeria* prfA gene. pGG49 was digested with NheI and SalI to remove the insert, which was ligated into XbaI and SalI-digested pDP2028 to yield pGG34.

pGG55 was then generated from pGG34 as follows: The human papilloma virus E7 gene was amplified by PCR using the primers 5'-GGCTCGAGCATGGAGATACACC-3' (SEQ ID NO: 1) and 5'-GGGGACTAGTTTATGGTTTCT-GAGAACA-3' (SEQ ID NO: 2), digested with XhoI and SpeI (New England Biolabs, Beverly, Mass.), and ligated into similarly digested pGG34, thereby fusing the E7 gene to the hly gene that is located upstream of XhoI. The resulting plasmid is pGG55 which contains a multi-gene cassette of hly, E7 antigen and prfA. The hly promoter drives the expression of the first 441 amino acids of the hly gene product, LLO, which is joined by the XhoI site to the E7 gene. By deleting the hemolytic C-terminus of LLO, the hemolytic activity of the fusion protein is neutralized. The pluripotent transcription factor, prfA, is also included on pGG-55 with its expression driven by its natural promoter. Generation of GG-L74

GG-L74 was created from *Listeria* strain 10403S by double allelic exchange at the orfZ domain, using a temperature-sensitive shuttle plasmid, as described in Gunn et al. (2001, J. Immunology 167: 6471-6479). GG-L74 was generated by introducing an expression cassette containing the hly-E7 fusion gene into the orfZ domain of the *L. monocytogenes* genome. The hly promoter drives the expression of the first 441 amino acids of the hly gene product, LLO, which is joined, by the XhoI site to the E7 gene. The result is a hly-E7 fusion gene that was transcribed and secreted as LLO-E7. The hly-E7 gene was ligated into the pKSV7 shuttle vector in the reverse orientation to avoid integration into the hly gene. The resulting plasmid, GG-L74, is an expression system that includes the previously described expression cassette inserted in the middle of a 1.6 Kb sequence that corresponds to the orfX, Y, Z domain of the *L. monocytogenes* genome. L. monocyto genes strain 10403S was transformed with pGG-74. The homology domains allow for insertion of the LLO-E7 gene cassette into the orfZ domain by homologous recombination as described in Gunn et al. (2001, J. Immunology 167: 6471-6479). Clones were screened for integration of the LLO-E7 gene cassette into the orfZ domain.

Experimental Design $2 \times 10^5$ TC-1 (ATCC, Manassas, Va.) were implanted subcutaneously in mice (n=8) and allowed to grow for about 7 days, after which tumors were palpable. TCl is a C57BL/6 epithelial cell line that was immortalized with HPV E6 and E7 and transformed with activated ras, which forms tumors upon subcutaneous implantation. Mice were immunized with the appropriate *Listeria* strain on days 7 and 14 following implantation of tumor cells. A non-immunized control group (naïve) was also included. Tumor growth was measured with electronic calipers.

Results

Two *Listeria* vaccine vectors, each expressing a fusion of a non-hemolytic LLO fragment to the E7 antigen of human papilloma virus from an episomal construct (GG-L55) or the *Listeria* chromosome (GG-L74) were evaluated for ability to induce immunity to tumors, prevent tumorigenesis and inhibit tumor growth in animals. GG-L55 and GGL74 has $LD_{50}$ in mice of $10^9$ and $10^6$ CFU, respectively. TC-1 cells were implanted subcutaneously in mice and allowed to grow until tumors were palpable (approximately 5 mm in size). Mice were then immunized with 0.1 $LD_{50}$ of GG-L55, GG-L74, or 0.001 $LD_{50}$ of GG-L55 (to determine the effect of immunizing load).

Figure 1B:
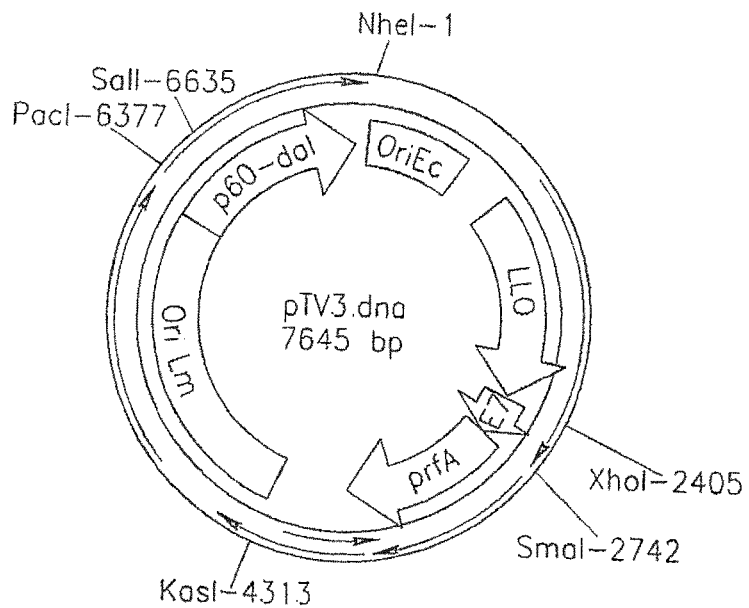

By day 28 following injection of TC-1 tumor cells, five of the eight animals that received GG-L55 were tumor-free and remained so until the end of the study. All of the naive animals and animals immunized with GG-L74 had large tumors. The animals receiving the smaller dose of GG-L55 grew tumors as well, but these were significantly smaller than those in the group immunized with GG-L74 (FIG. 1A-1B).

Thus, antigen constructs expressed from a plasmid confer stronger and more protective immune response than antigen constructs expressed from the *Listeria* chromosome.

Example 2

A Plasmid Containing an Amino Acid Metabolism Enzyme Instead of an Antibiotic Resistance Gene is Retained in *E. Coli* and LM Both In Vitro and In Vivo Materials and Experimental Methods Construction of Antibiotic Resistance Factor Free Plasmid pTV3

Construction of p60-dal cassette. The first step in the construction of the antibiotic resistance gene-free vector was construction of a fusion of a truncated p60 promoter to the dal gene. The LM alanine racemase (dal) gene (forward primer: 5'-CCA TGG TGA CAG GCT GGC ATC-3'; SEQ ID NO: 8) (reverse primer: 5'-GCT AGC CTA ATG GAT GTA TTT TCT AGG-3'; SEQ ID NO: 9) and a minimal p60 promoter sequence (forward primer: 5'-TTA ATT AAC AAA TAG TTG GTA TAG TCC-3'; SEQ ID No: 22) (reverse primer: 5'-GAC GAT GCC AGC CTG TCA CCA TGG AAA ACT CCT CTC-3'; SEQ ID No: 23) were isolated by PCR amplification from the genome of LM strain 10403S. The primers introduced a PacI site upstream of the p60 sequence, an NheI site downstream of the dal sequence (restriction sites in bold type), and an overlapping dal sequence (the first 18 bp) downstream of the p60 promoter for subsequent fusion of p60 and dal by splice overlap extension (SOE)-PCR. The sequence of the truncated p60 promoter was: CAAATAGTTGGTATAGTCCTCTTTAGCCTTTGGAGT-ATTATCTCATCATTTGTT TTTTAGGTGAAAACTGGG-TAAACTTAGTATTATCAATATAAAATTAATTCTCA AATACTTAATTACGTACTGGGATTTTCT-GAAAAAAGAGAGGAGTTTTCC (SEQ ID NO: 7, Kohler et al, J Bacteriol 173: 4668-74, 1991). Using SOE-PCR, the p60 and dal PCR products were fused and cloned into cloning vector pCR2.1 (Invitrogen, La Jolla, Calif.).

Removal of antibiotic resistance genes from pGG55. The subsequent cloning strategy for removing the Chloramphenicol acetyltransferase (CAT) genes from pGG55 and introducing the p60-dal cassette also intermittently resulted in the removal of the gram-positive replication region (ori-Rep; Brantl et al, Nucleic Acid Res 18: 4783-4790, 1990). In order to re-introduce the gram-positive oriRep, the oriRep was PCR-amplified from pGG55, using a 5'-primer that added a NarI/EheI site upstream of the sequence (GGCGC-CACTAACTCAACGCTAGTAG, SEQ ID NO: 10) and a 3'-primer that added a NheI site downstream of the sequence (GCTAGCCAGCAAAGAAAAACAAACACG, SEQ ID NO: 11). The PCR product was cloned into cloning vector pCR2.1 and sequence verified.

In order to incorporate the p60-dal sequence into the pGG55 vector, the p60-dal expression cassette was excised from pCR-p60dal by PacI/NheI double digestion. The replication region for gram-positive bacteria in pGG55 was amplified from pCR-oriRep by PCR (primer 1, 5'-GTC GAC GGT CAC CGG CGC CAC TAA CTC AAC GCT AGT AG-3'; SEQ ID No: 20); (primer 2, 5'-TTA ATT AAG CTA GCC AGC AAA GAA AAA CAA ACA CG-3'; SEQ ID No: 21) to introduce additional restriction sites for EheI and NheI. The PCR product was ligated into pCR2.1-TOPO (Invitrogen, Carlsbad, Calif.), and the sequence was verified. The replication region was excised by EheI/NheI digestion, and vector pGG55 was double digested with EheI and NheI, removing both CAT genes from the plasmid simultaneously.

The two inserts, p60-dal and oriRep, and the pGG55 fragment were ligated together, yielding pTV3.

Preparation of DNA for Real-Time PCR

Total *Listeria* DNA was prepared using the Masterpure Total DNA kit (Epicentre, Madison, Wis.). Briefly, *Listeria* were cultured for 24 hours at 37° C. and shaken at 250 rpm in 25 ml of Luria-Bertoni broth (LB). Bacterial cells were pelleted by centrifugation, resuspended in PBS supplemented with 5 mg/ml of lysozyme and incubated for 20 minutes at 37° C., after which DNA was isolated.

In order to obtain standard target DNA for real-time PCR, the LLO-E7 gene was PCR amplified from pGG55 (5'-ATGAAAAAAATAATGCTAGTTTTTATTAC-3' (SEQ ID NO: 12); 5'-GCGGCCGCTTAATGATGATGATGATGAT-GTGGTTTCTG AGAACAGATG-3' (SEQ ID NO: 13)) and cloned into vector pETblue1 (Novagen, San Diego, Calif.). Similarly, the plcA amplicon was cloned into pCR2.1. *E. coli* were transformed with pET-LLOE7 and pCR-plcA, respectively, and purified plasmid DNA was prepared for use in real-time PCR.

Real-Time PCR

Taqman primer-probe sets (Applied Biosystems, Foster City, Calif.) were designed using the ABI PrimerExpress software (Applied Biosystems) with E7 as a plasmid target, using the following primers: 5'-GCAAGTGTGACTC-TACGCTTCG-3' (SEQ ID NO: 14); 5'-TGCCCATTAACA-GGTCTTCCA-3' (SEQ ID NO: 15); 5'-FAM-TGCGTA CAAAGCACACACGTAGACATTCGTAC-TAMRA-3' (SEQ ID NO: 16) and the one-copy gene plcA (TGACATCGTTTGTGTTTGAGCTAG-3' (SEQ ID NO: 17), 5'-GCAGCGCTCTCTATACCAGGTAC-3' (SEQ ID NO: 18); 5'-TET-TTAATGTCCATGTTA TGTCTCCGT-TATAGCTCATCGTA-TAMRA-3'; SEQ ID NO: 19) as a *Listeria* genome target.

0.4 µM primer and 0.05 mM probe were mixed with PuRE Taq RTG PCR beads (Amersham, Piscataway, N.J.) as recommended by the manufacturer. Standard curves were prepared for each target with purified plasmid DNA, pET-LLOE7 and pCR-plcA (internal standard) and used to calculate gene copy numbers in unknown samples. Mean ratios of E7 copies/plcA copies were calculated based on the standard curves and calibrated by dividing the results for Lmdd-TV3 and Lm-LLOE7 with the results from Lm-E7, a *Listeria* strain with a single copy of the E7 gene integrated into the genome. All samples were run in triplicate in each qPCR assay which was repeated three times. Variation between samples was analyzed by Two-Way ANOVA using the KyPlot software. Results were deemed statistically significant if $p<0.05$.

Growth Measurements

Bacteria were grown at 37° C., 250 rpm shaking in Luria Bertani (LB) Medium+/−100 micrograms (µg)/ml D-alanine and/or 37 µg/ml chloramphenicol. The starting inoculum was adjusted based on $OD_{600}$ nm measurements to be the same for all strains.

Results

Figure 2:
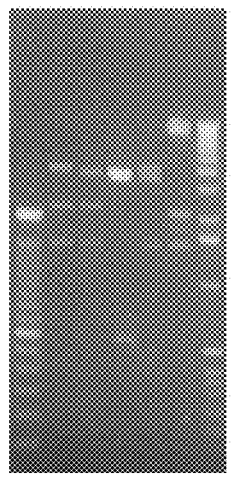
FIG. 2: Plasmid preparation of pTV3 from *E. coli* strain MB2159. Qiagen® midi-preparation of nucleic acids was following the manufacturer's protocol. Lanes from left to right: Lanes 1 and 7: Molecular Weight Marker, 100Bp ladder (Invitrogen). Lane 2: pTV3, clone #15. Lane 3: pTV3, clone #16. Lane 4: pTV3C, clone #22. Lane 5: pTV3C, clone #24. Lane 6: pGG55 control.

An auxotroph complementation system based on D-alanine racemase was utilized to mediate plasmid retention in LM without the use of an antibiotic resistance gene. *E. coli* strain MB2159 is an alr (−)/dadX (−) deficient mutant that is not able to synthesize D-alanine racemase. *Listeria* strain Lm dal(−)/dat(−) (Lmdd) similarly is not able to synthesize D-alanine racemase due to partial deletions of the dal and the dat genes. Plasmid pGG55, which is based on *E. coli*-*Listeria* shuttle vector pAM401, was modified by removing both CAT genes and replacing them with a p60-dal expression cassette under control of the *Listeria* p60 promoter, as described in the Methods section (FIG. 1A-1B). DNA was purified from several colonies (FIG. 2).

Figure 3A:
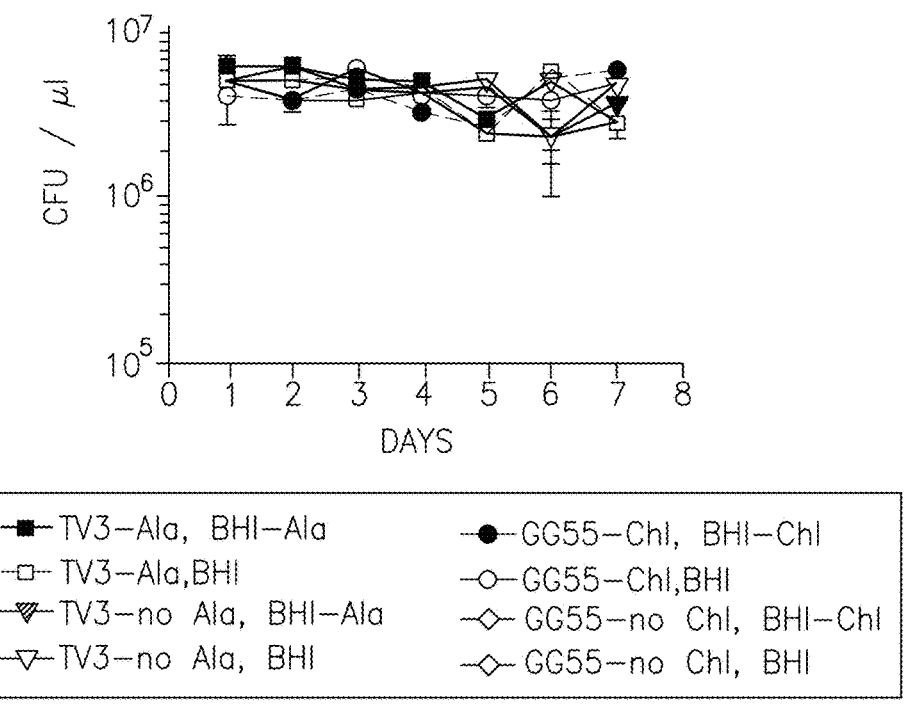
FIG. 3A-3B. Plasmid maintenance in vitro (FIG. 3A) and in vivo (FIG. 3B). To determine in vitro stability, strains were cultured with (GG55-Chl) and without (GG55-no Chl) chloramphenicol (LM-LLO-E7) or with and without D-alanine [Lmdd(pTV3)]. The cultures were diluted 1:1000 daily into fresh LB. The CFU of the cultures were determined daily on BHI (BHI) and on BHI with chloramphenicol (BHI-Chl) for LM-LLO-E7 or on BHI with D-alanine (BHI-Ala) for Lmdd(pTV3). All liquid medium and plates contained an additional 50 µg of streptomycin per ml, to which *Listeria monocytogenes* strain 10403S is naturally resistant. To determine in vivo plasmid maintenance, LM was injected intraperitoneally at a dose of 1/10 the LD50 in5O C57BL/6 mice. Spleens were harvested at different time points post-injection and homogenized in phosphate-buffered saline (PBS). CFU counts were prepared on BHI plates with and without D-alanine for Lmdd(pTV3), on BHI plates with and without chloramphenicol for LM-LLO-E7, and on BHI plates only for wild-type 10403S.

To determine plasmid stability in vitro, LM-LLO-E7 and Lmdd(pTV3) were cultured for 70 generations in the presence and absence of selective pressure. CFU were determined daily on selective and nonselective plates for each culture. In this system, plasmid loss results in a greater number of colonies growing on nonselective plates (BHI plus D-alanine for Lmdd(pTV3), BHI only for LM-LLO-E7) versus selective plates (BHI only for Lmdd(pTV3), BHI plus chloramphenicol for LM-LLO-E7). No difference in CFU was detected between nonselective and selective plates (FIG. 3A), indicating stable maintenance of the plasmid throughout the culture for at least 70 generations, when the experiment was terminated.

Figure 3B:
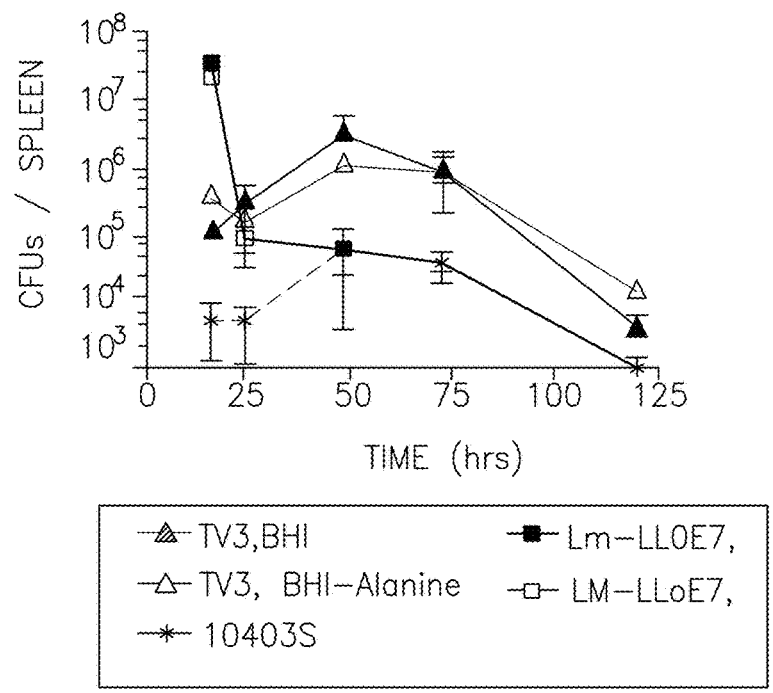
Figures 5, 5A, 5B, 5C, 5D:
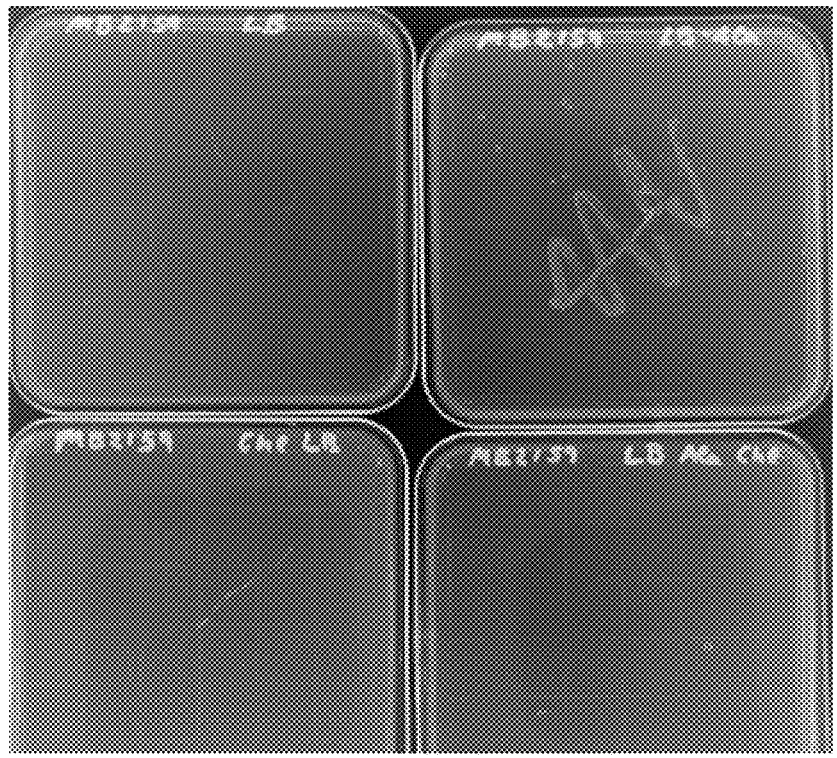
FIG. 5A-5D depicts growth on LB-agar plates of *E. coli* strain MB2159 (alanine racemace negative) without the pTV3 vector. Agar plates are arranged as in FIG. 5 FIG. 5A Upper left: MB2159 does not grow.
Figures 6, 6A:
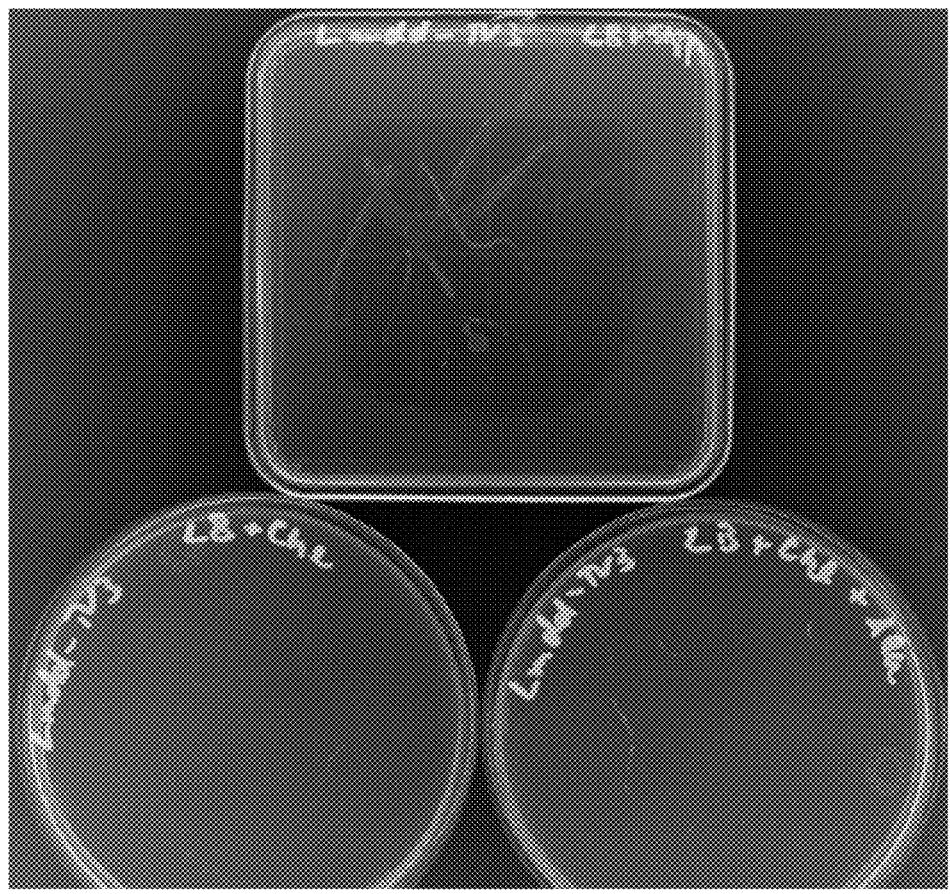

In addition, plasmid stability in vivo was tested in C57BL/6 mice by isolating viable bacteria at different time points after injection. Again, CFU counts on selective and nonselective plates were used to determine plasmid maintenance among the isolated bacteria (FIG. 3B). No differences in CFU were detected on selective and nonselective plates for each construct, indicating the stable presence of the recombinant plasmid in all bacteria isolated. Since viable Lmdd(pTV3) bacteria were isolated at least until day 5, plasmid loss in vivo followed by early clearance of injected bacteria could be excluded as a possible reason for the low virulence observed for Lmdd(pTV3) bacteria (Example 3).

In summary, pTV3 was stably maintained in *E. coli* as well as in *Listeria*, both in vitro and in vivo. Bacterial growth on LB media that was not supplemented with additional D-alanine indicated that the dal expression cassette was active also in gram-negative *E. coli*. Both *E. coli*-pTV3 and Lmdd-pTV3 remained sensitive to chloramphenicol, indicating the successful removal of both CAT genes from the plasmid. Representative plates are depicted in FIGS. 4-7.

The pTV3 copy number per cell was compared between Lm-LLOE7 in the presence of chloramphenicol and Lmdd-TV3 in the absence of chloramphenicol by real-time PCR of the E7 sequences, in both *Listeria* and *E. coli*. Lm-LLOE7 expresses LLO/E7 fusion protein from pGG55. Plasmid copy numbers of Lmdd-TV3 and Lm-LLOE7 did not significantly differ from one another, showing stable retention of plasmid pTV3 in both *Listeria* and *E. coli*.

Figure 8:
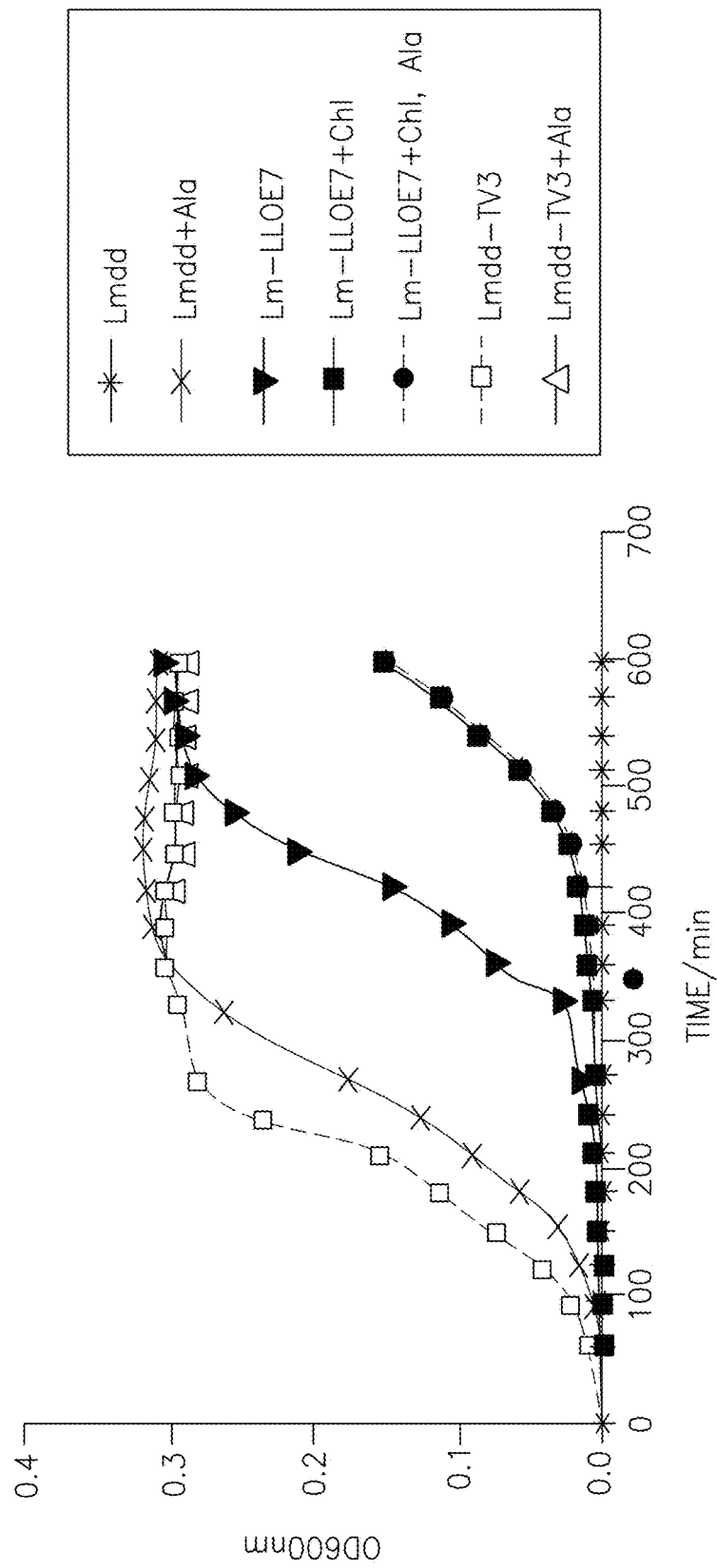
FIG. 8 depicts bacterial growth as measured by optical density (600 nanometers [nm]) plotted vs. time. +Ala: media contains D-alanine; +Chl: media contains chloramphenicol.

In order to verify the complementation of bacterial functions, in vitro growth kinetics were compared among Lmdd, Lmdd-TV3 and Lm-LLOE7. Lmdd-TV3, but not non-complemented Lmdd was able to grow in alanine-free media (FIG. 8). In fact, Lmdd-TV3 reached logarithmic growth phase sooner than both Lm-LLOE7 and Lmdd complemented with exogenous D-alanine. This growth attenuation of Lm-LLOE7 was partially due to the metabolic burden of CAT expression. However, even in the absence of chloramphenicol, Lm-LLOE7 still grew more slowly in vitro than Lmdd-TV3.

Example 3

Plasmids Containing a Metabolic Enzyme do not Increase the Virulence of Bacteria Materials and Experimental Methods Hemolytic Lysis Assay $4 \times 10^9$ CFU of *Listeria* were thawed, pelleted by centrifugation (1 minute, 14000 rpm) and resuspended in 100 µl PBS, pH 5.5 with 1 M cysteine. Bacteria were serially diluted 1:2 and incubated for 45 minutes at 37° C. in order to activate secreted LLO. Defibrinated total sheep blood (Cedarlane, Hornby, Ontario, Canada) was washed twice with 5 volumes of PBS and three to four times with 6 volumes of PBS-Cysteine until the supernatant remained clear, pelleting cells at 3000×g for 8 minutes between wash steps, then resuspended to a final concentration of 10% (v/v) in PBS-Cysteine. 100 µl of 10% washed blood cells were mixed with 100 µl of *Listeria* suspension and incubated for additional 45 minutes at 37° C. Un-lysed blood cells were then pelleted by centrifugation (10 minutes, 1000×g). 100 µl of supernatant was transferred into a new plate and the $OD_{530nm}$ was determined and plotted against the sample dilution.

Results

As virulence is linked to LLO function, the hemolytic lysis activity between Lmdd-TV3 and Lm-LLOE7 was compared. This assay tests LLO function by lysis of red blood cells and can be performed with culture supernatant, purified LLO or bacterial cells. Lmdd-TV3 displayed higher hemolytic lysis activity than Lm-LLOE7.

In vivo virulence was also measured by determining LD50 values, a more direct, and therefore accurate, means of measuring virulence. The LD50 of Lmdd-TV3 ($0.75 \times 10^9$) was very close to that of Lm-LLOE7 ($1 \times 10^9$), showing that plasmids containing a metabolic enzyme do not increase the virulence of bacteria.

Example 4

Vaccine Strains Carrying Plasmids Containing a Metabolic Enzyme Mediate Antigen Expression Antigen expression from the metabolic enzyme-containing plasmid was tested in vitro by Western blot. When analyzing equal amounts of total protein from bacterial culture supernatants, Lmdd-TV3 cultures contained approximately double the amount of total antigen than Lm-LLOE7 cultures. This difference may be a result of a higher overall metabolic load in Lm-LLOE7, due to the larger size of the plasmid (12.8 kB) compared to Lmdd-TV3 (7.6 kB).

Thus, metabolic enzymes can be used instead of antibiotic resistance genes to mediate plasmid retention in auxtrophic bacteria. Further, such plasmids have utility in expression of heterologous proteins in bacteria.

Example 5

Induction of Anti-Tumor Immunity by Plasmids Containing a Metabolic Enzyme

Figure 9A:
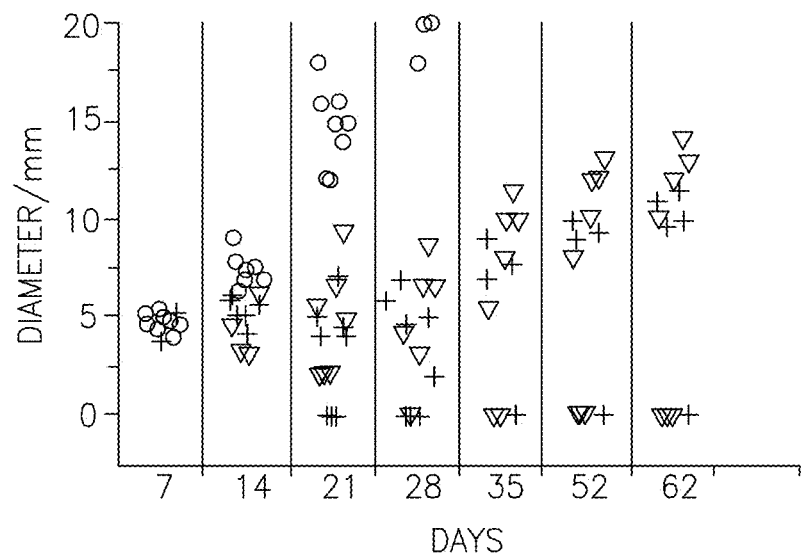
FIG. 9A-9B depicts two separate experiments (FIG. 9A and FIG. 9B) showing that immunization of mice with Lmdd-TV3 and Lm-LLO-E7 resulted in similar tumor regression with no statistically significant difference ($p<0.05$) between the vaccinated groups. Circles represent naive mice, inverted triangles represent mice administered Lmdd-TV3, and crosses represent mice administered Lm-LLOE7.
Figure 9B:
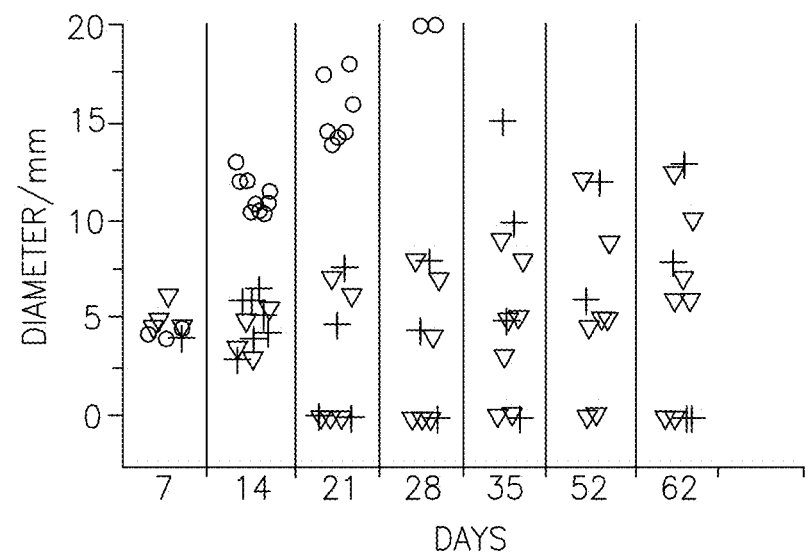

Efficacy of the metabolic enzyme-containing plasmid as a cancer vaccine was determined in a tumor regression model, as described in Example 1. The TC-1 cell line model, which is well characterized for HPV vaccine development and which allowed for a controlled comparison of the regression of established tumors of similar size after immunization with Lmdd-TV3 or Lm-LLOE7, was used. In two separate experiments, immunization of mice with Lmdd-TV3 and Lm-LLOE7 resulted in similar tumor regression (FIG. 9A-9B) with no statistically significant difference (p<0.05) between vaccinated groups. All immunized mice were still alive after 63 days, whereas non-immunized mice had to be sacrificed when their tumors reached 20 mm diameter. Cured mice remained tumor-free until the termination of the experiment.

Thus, metabolic enzyme-containing plasmids are efficacious as a therapeutic cancer vaccine. Because immune responses required for a therapeutic cancer vaccine are stronger than those required for a prophylactic cancer vaccine, these results demonstrate utility as well for a prophylactic cancer vaccine.

Example 6

Plasmids Containing a Metabolic Enzyme Induce Antigen-Specific, Tumor Infiltrating T-Cells Materials and Experimental Methods T-Cell Analysis T-cells from spleen and tumor infiltrating T-cells were analyzed for CD8 and CD4 surface markers and E7 specificity according to standard protocols (Gunn et al. (2001, J. Immunol, 167: 6471-6479). C57BL/6 mice were immunized ip. 7 and 14 days after tumor implantation with Lmdd-TV3 or Lm-LLOE7. Splenocytes and tumors were harvested 5 days after the second injection, and were stained at room temperature with H-2D$^b$ tetramers loaded with the E7 peptide (RAHYNIVTF, SEQ ID NO: 19) or a control (HIV-Gag) peptide at a 1:200 dilution. Tetramers were provided by the National Institute of Allergy and Infectious Diseases Tetramer Core Facility and the National Institutes of Health AIDS Research and Reference Reagent Program.

Three-color flow cytometry for CD8 (53-6.7, PE conjugated), and E7 H-2D$^b$ tetramer was performed using a FACSCalibur® flow cytometer with CellQuest® software (Becton Dickinson, Mountain View, Calif.). Intracellular gamma interferon (IFN-) staining was performed on a second subset of cells. Before staining for the cell surface antigens and IFN-production, lymphocytes were stimulated in vitro by culturing in the presence of monensin (BD Biosciences) to accumulate intracellular IFN-γ in the Golgi apparatus. After culture for 5 hr in RP-10 supplemented with interleukin-2 (50 U/ml) and 1 µl of brefeldin A (monensin) per ml, the cells were surface stained for effector markers at 4° C. for 20 min with phycoerythrin-conjugated anti-CD8 (PharMingen) and antigen-presenting cell-conjugated MEL-14 (anti-CD62 ligand). Cells were gated on (selected for) CD62 ligand low to select activated cells before being analyzed for CD8$^+$ IFN-+ populations.

Results

Anti-tumor efficacy of a vaccine is often linked to its ability to induce antigen-specific, tumor-infiltrating lymphocytes. To further characterize Lmdd-TV3 efficacy, the tumor-infiltrating cytotoxic T-cells (CTL) for E7 antigen specificity were therefore analyzed. Both Lmdd-TV3 and Lm-LLOE7 induce a significant percentage of E7 tetramer specific T-cells infiltrating the tumor (Table 1). No significant differences were observed in the percentages of IFN-γ-producing CD8$^+$ T cells in *L. monocytogenes* LLO-E7-immunized mice versus Lmdd(pTV3)-treated mice. Thus, both Lmdd-TV3 and Lm-LLOE7 induced tumor infiltrating, antigen-specific CTL that controlled tumor growth.

| Group | Dose | CD8+, E7-tetamer+, CD62−; Experiment A | CD8+, E7-tetamer+, CD62− Experiment B |
|---|---|---|---|
| Naïve | 0 | 8.81 | 4.86 |
| Lmdd-TV3 | 0.75 × 10$^8$ | 20.72 | 14.86 |
| Lm-LLOE7 | 1 × 10$^8$ | 27.43 | 20.82 |

Table 1: Groups of three mice were injected with 1×10$^5$ TC-1 tumor cells in a matrigel suspension on day. Cells were stained with anti-CD8– antibody and E7-tetramer and subjected to FACS analysis. After gating on (selecting) CD8+/E7-tetramer+/CD62−, the percentage of CD8+/E7-tetramer+/CD62− cells from total live cells was calculated.

Example 7

Chromosomal Integration of Recombinant Genes Based on Phage Integration System

A shuttle plasmid is constructed containing (1) a replication gene for *E. coli*, (2) a PSA attPP' integration site, (3) a *Listeria* dal gene under the control of its natural promoter, and (4) a PSA integrase gene under the control of the *Listeria* p60 promoter. The skilled artisan will appreciate that other promoters or polycistronic expression cassettes may be used to drive the expression of the introduced genes, in particular the dal gene and the PSA integrase gene. The PSA integrase gene and the PSA attPP' integration site from pPL2 (Lauer et al., 2002, J Bacteriol, 2002. 184: 4177-4186) is modified by PCR to contain restriction sites at the 5'-end and the 3'-end that are compatible with cloning these nucleic acids into shuttle plasmid pTV3. During this step, the *Listeria* replication region from pTV3 is removed, resulting in plasmid pTV6. This plasmid contains replication functions for its amplification in *E. coli*, a dal gene for complementation of dal auxotroph *E. coli* and *Listeria*, and integration functions (PSA integrase, attPP' site) for integration of the plasmid into the *Listeria* genome. The plasmid is amplified in dal auxotroph *E. coli* strain MB2159 (Strych et al), isolated, and subsequently electroporated into *Listeria*.

Alternatively, instead of wild-type LM strain 10403S, dal auxotroph Lmdal(−) dat(−) (previous Examples) is used as a host strain. Because the plasmid does not contain a *Listeria* replication region, only *Listeria* that contain a copy that is integrated into the genome are selected upon growth in LB media.

In summary, this invention allows the replacement of selection with antibiotics with selection that utilizes complementation of auxotroph mutant strains. The skilled artisan will appreciate that other auxotroph strains and complementation systems may be adopted for the use with this invention.

Example 8

Creation of a General Shuttle Vector Based on pTV3 pTV3 is digested with KasI or EheI and AatII, removing the prfA gene, the LLO-E7 fusion gene, and most of the LLO promoter. A multiple cloning site consisting of BamHI, XhoI, XbaI, NotI, SpeI, SmaI, and SacI is introduced by ligating the following paired oligonucleotides to the vector backbone:

(SEQ ID No: 24)
5'-CGG ATC CCT CGA GCT CAG AGC GGC CGC ACT AGT CCC GGG GAG CTC G.

5'-TCG ACG AGC TCC CCG GGA CTA GTG CGG CCG CTC TGA GCT CGA GGG ATC CGA CGT (SEQ ID No: 25; overhanging ends that are compatible with the vector sites restricted with AatI and SalI are in italics).

An antigen cassette of interest is then ligated into the multiple cloning site. The plasmid is then used to create a vaccine strain expressing the antigen encoded therein.

Example 9

Creation of a General Shuttle Vector Based on an Expression Plasmid

The p60-dal expression cassette (Example 2) is introduced into an expression plasmid. For example, a commercial plasmid (e.g. pCR2.1) may be used. Subsequently, the antibiotic resistance genes are removal from the plasmid. The plasmid is then used to create a vaccine strain expressing the antigen encoded therein.

What is claimed is:

1. A method of inducing an immune response against an antigen-expressing tumor or a n antigen-expressing cancer in a subject, said method comprising the step of administering to the subject a recombinant *Listeria* strain auxotrophic for D-alanine synthesis, comprising a mutation in a D-alanine racemase gene and in a D-amino acid transferase gene in the chromosome of said recombinant *Listeria*, wherein said *Listeria* further comprises a plasmid, wherein the plasmid comprises:
    a first nucleic acid sequence encoding a polypeptide, wherein said polypeptide comprises a heterologous antigen, and
    a second nucleic acid sequence encoding a D-alanine racemase enzyme, wherein said plasmid does not confer antibiotic resistance upon said recombinant *Listeria* strain,
    whereby said D-alanine racemase gene complements said mutation in said chromosome of said recombinant *Listeria*, wherein said plasmid is stably maintained in said recombinant *Listeria* strain in the absence of an antibiotic selection, wherein said first nucleic acid sequence is operably linked to a prokaryotic promoter/regulatory sequence, and wherein said administering induces an immune response against said antigen-expressing tumor or said antigen-expressing cancer in said subject.

2. The method of claim 1, wherein said polypeptide is a fusion protein comprising said heterologous antigen and an additional polypeptide, wherein said additional polypeptide is a non-hemolytic fragment of a listeriolysin O (LLO) protein, a Proline, Glutamic acid, Serine and Threonine (PEST) amino acid sequence, or an Actin assembly-inducing protein (ActA) protein or a fragment thereof.

3. The method of claim 1, wherein said second nucleic acid sequence is operably linked to said promoter/regulatory sequence.

4. The method of claim 1, wherein said heterologous antigen is an HPV E6 or an HPV E7 antigen.

5. The method of claim 1, wherein said cancer is a cervical cancer.

6. The method of claim 1, wherein said immune response comprises reducing the size of a HPV antigen-expressing tumor or a HPV antigen-expressing cancer, protecting against recurrence of a HPV antigen-expressing tumor or a HPV antigen-expressing cancer, reducing the growth rate of a HPV antigen-expressing tumor or a HPV antigen-expressing cancer, or inhibiting the growth rate of a HPV antigen-expressing tumor or a HPV antigen-expressing cancer, or any combination thereof.

7. The method of claim 6, wherein said immune response comprises treating said HPV antigen-expressing tumor or said HPV antigen-expressing cancer.

8. The method of claim 7, wherein treating said HPV antigen-expressing tumor or said HPV antigen-expressing cancer comprises regression of an established HPV antigen-expressing tumor or an established HPV-expressing cancer.

9. The method of claim 1, wherein said inducing an immune response comprises inducing a HPV antigen-specific tumor-infiltrating cytotoxic T-cells (CTL).

10. A method of regressing an antigen-expressing tumor or an antigen-expressing cancer in a subject, said method comprising the step of administering to the subject a recombinant *Listeria* strain auxotrophic for D-alanine synthesis, comprising a mutation in a D-alanine racemase gene and in a D-amino acid transferase gene in the chromosome of said recombinant *Listeria*, wherein said *Listeria* further comprises a plasmid, wherein the plasmid comprises:

a first nucleic acid sequence encoding a polypeptide, wherein said polypeptide comprises a heterologous antigen, and a second nucleic acid sequence encoding a D-alanine racemase enzyme, wherein said plasmid does not confer antibiotic resistance upon said recombinant *Listeria* strain, whereby said D-alanine racemase gene complements said mutation in said chromosome of said recombinant *Listeria*, wherein said plasmid is stably maintained in said recombinant *Listeria* strain in the absence of an antibiotic selection, and wherein said first nucleic acid sequence is operably linked to a prokaryotic promoter/regulatory sequence, wherein said administering regresses said antigen-expressing tumor or said antigen-expressing cancer in said subject.

11. The method of claim 10, wherein said polypeptide is a fusion protein comprising said heterologous antigen and an additional polypeptide, wherein said additional polypeptide is a non-hemolytic fragment of a listeriolysin O (LLO) protein, a Proline, Glutamic acid, Serine and Threonine (PEST) amino acid sequence, or an Actin assembly inducing protein (ActA) protein or a fragment thereof.

12. The method of claim 10, wherein said second nucleic acid sequence is operably linked to said promoter/regulatory sequence.

13. The method of claim 10, wherein said heterologous antigen is an HPV E6 or an HPV E7 antigen.

14. The method of claim 10, wherein said cancer is a cervical cancer.

15. The method of claim 10, wherein said regressing said antigen-expressing tumor or said antigen-expressing cancer comprises reducing the size of a HPV antigen-expressing tumor or a HPV antigen-expressing cancer, reducing the growth rate of a HPV antigen-expressing tumor or a HPV antigen-expressing cancer, or inhibiting the growth rate of a HPV antigen-expressing tumor or a HPV antigen-expressing cancer, or any combination thereof.

16. The method of claim 15, wherein said regressing said HPV antigen-expressing tumor or said HPV antigen-expressing cancer comprises treating said tumor or said cancer.

17. The method of claim 15, wherein said regressing said HPV antigen-expressing tumor or said HPV antigen-expressing cancer comprises inducing an immune response against said HPV antigen-expressing tumor or said HPV antigen-expressing cancer.

18. The method of claim 17, wherein said inducing an immune response comprises inducing HPV antigen-specific tumor-infiltrating cytotoxic T-cells (CTL).

* * * * *

UNITED STATES PATENT AND TRADEMARK OFFICE
CERTIFICATE OF CORRECTION

PATENT NO. : 9,700,608 B2
APPLICATION NO. : 15/296973
DATED : July 11, 2017
INVENTOR(S) : Yvonne Paterson et al.

Page 1 of 1

It is certified that error appears in the above-identified patent and that said Letters Patent is hereby corrected as shown below:

In the Specification

Please replace Lines 14-21 in Column 1 with the following:
GOVERNMENT INTEREST STATEMENT
This invention was made with government support under grant number CA069632 awarded by the National Institutes of Health. The government has certain rights in the invention.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 26

<210> SEQ ID NO 1
<211> LENGTH: 22
<212> TYPE: DNA
<213> ORGANISM: Artificial
<220> FEATURE:
<223> OTHER INFORMATION: Primer

<400> SEQUENCE: 1
ggctcgagca tggagataca cc                                              22

<210> SEQ ID NO 2
<211> LENGTH: 28
<212> TYPE: DNA
<213> ORGANISM: Artificial
<220> FEATURE:
<223> OTHER INFORMATION: Primer
```

```
<400> SEQUENCE: 2
ggggactagt ttatggtttc tgagaaca                                    28

<210> SEQ ID NO 3
<211> LENGTH: 31
<212> TYPE: DNA
<213> ORGANISM: Artificial
<220> FEATURE:
<223> OTHER INFORMATION: Primer

<400> SEQUENCE: 3
gggggctagc cctcctttga ttagtatatt c                                31

<210> SEQ ID NO 4
<211> LENGTH: 28
<212> TYPE: DNA
<213> ORGANISM: Artificial
<220> FEATURE:
<223> OTHER INFORMATION: Primer

<400> SEQUENCE: 4
ctccctcgag atcataattt acttcatc                                    28

<210> SEQ ID NO 5
<211> LENGTH: 55
<212> TYPE: DNA
<213> ORGANISM: Artificial
<220> FEATURE:
<223> OTHER INFORMATION: Primer

<400> SEQUENCE: 5
gactacaagg acgatgaccg acaagtgata acccgggatc taaataaatc cgttt      55

<210> SEQ ID NO 6
<211> LENGTH: 27
<212> TYPE: DNA
<213> ORGANISM: Artificial
<220> FEATURE:
<223> OTHER INFORMATION: Primer

<400> SEQUENCE: 6
cccgtcgacc agctcttctt ggtgaag                                     27

<210> SEQ ID NO 7
<211> LENGTH: 156
<212> TYPE: DNA
<213> ORGANISM: Listeria monocytogenes

<400> SEQUENCE: 7
caaatagttg gtatagtcct ctttagcctt tggagtatta tctcatcatt tgtttttag   60 gtgaaaactg ggtaaactta gtattatcaa tataaaatta attctcaaat acttaattac 120
gtactgggat tttctgaaaa aagagaggag ttttcc                          156

<210> SEQ ID NO 8
<211> LENGTH: 21
<212> TYPE: DNA
<213> ORGANISM: Artificial
<220> FEATURE:
<223> OTHER INFORMATION: Primer

<400> SEQUENCE: 8
ccatggtgac aggctggcat c                                           21
```

```
<210> SEQ ID NO 9
<211> LENGTH: 27
<212> TYPE: DNA
<213> ORGANISM: Artificial
<220> FEATURE:
<223> OTHER INFORMATION: Primer

<400> SEQUENCE: 9
gctagcctaa tggatgtatt ttctagg                                        27

<210> SEQ ID NO 10
<211> LENGTH: 25
<212> TYPE: DNA
<213> ORGANISM: Artificial
<220> FEATURE:
<223> OTHER INFORMATION: Primer

<400> SEQUENCE: 10
ggcgccacta actcaacgct agtag                                          25

<210> SEQ ID NO 11
<211> LENGTH: 27
<212> TYPE: DNA
<213> ORGANISM: Artificial
<220> FEATURE:
<223> OTHER INFORMATION: Primer

<400> SEQUENCE: 11
gctagccagc aaagaaaaac aaacacg                                        27

<210> SEQ ID NO 12
<211> LENGTH: 29
<212> TYPE: DNA
<213> ORGANISM: Artificial
<220> FEATURE:
<223> OTHER INFORMATION: Primer

<400> SEQUENCE: 12
atgaaaaaaa taatgctagt ttttattac                                      29

<210> SEQ ID NO 13
<211> LENGTH: 48
<212> TYPE: DNA
<213> ORGANISM: Artificial
<220> FEATURE:
<223> OTHER INFORMATION: Primer

<400> SEQUENCE: 13
gcggccgctt aatgatgatg atgatgatgt ggtttctgag aacagatg                 48

<210> SEQ ID NO 14
<211> LENGTH: 22
<212> TYPE: DNA
<213> ORGANISM: Artificial
<220> FEATURE:
<223> OTHER INFORMATION: Primer

<400> SEQUENCE: 14
gcaagtgtga ctctacgctt cg                                             22

<210> SEQ ID NO 15
<211> LENGTH: 21
<212> TYPE: DNA
<213> ORGANISM: Artificial
<220> FEATURE:
<223> OTHER INFORMATION: Primer
```

<400> SEQUENCE: 15
tgcccattaa caggtcttcc a                                              21

<210> SEQ ID NO 16
<211> LENGTH: 32
<212> TYPE: DNA
<213> ORGANISM: Artificial
<220> FEATURE:
<223> OTHER INFORMATION: Primer

<400> SEQUENCE: 16
tgcgtacaaa gcacacacgt agacattcgt ac                                  32

<210> SEQ ID NO 17
<211> LENGTH: 24
<212> TYPE: DNA
<213> ORGANISM: Artificial
<220> FEATURE:
<223> OTHER INFORMATION: Primer

<400> SEQUENCE: 17
tgacatcgtt tgtgtttgag ctag                                           24

<210> SEQ ID NO 18
<211> LENGTH: 23
<212> TYPE: DNA
<213> ORGANISM: Artificial
<220> FEATURE:
<223> OTHER INFORMATION: Primer

<400> SEQUENCE: 18
gcagcgctct ctataccagg tac                                            23

<210> SEQ ID NO 19
<211> LENGTH: 38
<212> TYPE: DNA
<213> ORGANISM: Artificial
<220> FEATURE:
<223> OTHER INFORMATION: Primer

<400> SEQUENCE: 19
ttaatgtcca tgttatgtct ccgttatagc tcatcgta                            38

<210> SEQ ID NO 20
<211> LENGTH: 38
<212> TYPE: DNA
<213> ORGANISM: Artificial
<220> FEATURE:
<223> OTHER INFORMATION: Primer

<400> SEQUENCE: 20
gtcgacggtc accggcgcca ctaactcaac gctagtag                            38

<210> SEQ ID NO 21
<211> LENGTH: 33
<212> TYPE: DNA
<213> ORGANISM: Artificial
<220> FEATURE:
<223> OTHER INFORMATION: Primer

<400> SEQUENCE: 21
ttaattaagc tagccagcaa agaaaaacaa aca                                 33

<210> SEQ ID NO 22
<211> LENGTH: 27

```
<212> TYPE: DNA
<213> ORGANISM: Artificial
<220> FEATURE:
<223> OTHER INFORMATION: Primer

<400> SEQUENCE: 22
ttaattaaca aatagttggt atagtcc                                        27

<210> SEQ ID NO 23
<211> LENGTH: 36
<212> TYPE: DNA
<213> ORGANISM: Artificial
<220> FEATURE:
<223> OTHER INFORMATION: Primer

<400> SEQUENCE: 23
gacgatgcca gcctgtcacc atggaaaact cctctc                              36

<210> SEQ ID NO 24
<211> LENGTH: 46
<212> TYPE: DNA
<213> ORGANISM: Artificial
<220> FEATURE:
<223> OTHER INFORMATION: Primer

<400> SEQUENCE: 24
cggatccctc gagctcagag cggccgcact agtcccgggg agctcg                   46

<210> SEQ ID NO 25
<211> LENGTH: 54
<212> TYPE: DNA
<213> ORGANISM: Artificial
<220> FEATURE:
<223> OTHER INFORMATION: Primer

<400> SEQUENCE: 25
tcgacgagct ccccgggact agtgcggccg ctctgagctc gagggatccg acgt          54

<210> SEQ ID NO 26
<211> LENGTH: 9
<212> TYPE: PRT
<213> ORGANISM: Human papillomavirus

<400> SEQUENCE: 26

Arg Ala His Tyr Asn Ile Val Thr Phe
1               5
```